US006818450B2

(12) United States Patent
Eaton et al.

(10) Patent No.: US 6,818,450 B2
(45) Date of Patent: Nov. 16, 2004

(54) USE OF INFRARED SPECTROSCOPY FOR ON-LINE PROCESS CONTROL AND ENDPOINT DETECTION

(75) Inventors: David R. Eaton, Kirkwood, MO (US); Walter Gavlick, Chesterfield, MO (US); Gary Klopf, Grover, MO (US); Arnold Hershman, Frontenac, MO (US); Denis Forster, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/150,030

(22) Filed: May 17, 2002

(65) Prior Publication Data

US 2002/0197725 A1 Dec. 26, 2002

Related U.S. Application Data

(60) Provisional application No. 60/292,659, filed on May 22, 2001.

(51) Int. Cl.[7] .......................... C12P 33/00; C12P 13/00; C12P 13/02; C12P 11/00; C07F 9/22

(52) U.S. Cl. ......................... 436/52; 436/128; 436/129; 436/130; 560/155; 560/171; 562/16; 562/17; 562/609; 568/448

(58) Field of Search .......................... 436/52, 128, 129, 436/130; 560/155, 171; 562/16, 17, 609; 568/448

(56) References Cited

U.S. PATENT DOCUMENTS

| | | |
|---|---|---|
| 3,799,758 A | 3/1974 | Franz et al. |
| 3,950,402 A | 4/1976 | Franz |
| 3,969,398 A | 7/1976 | Hershman |
| 4,454,043 A | 6/1984 | Ting et al. |
| 4,582,650 A | 4/1986 | Felthouse |
| 4,624,937 A | 11/1986 | Chou |
| 4,696,772 A | 9/1987 | Chou |
| 5,179,228 A | 1/1993 | Ramon et al. |
| 5,606,107 A | 2/1997 | Smith |

(List continued on next page.)

FOREIGN PATENT DOCUMENTS

| | | |
|---|---|---|
| WO | WO 96/40592 | 12/1996 |
| WO | WO 99/43430 | 9/1999 |
| WO | WO 00/01707 | 1/2000 |

OTHER PUBLICATIONS

US 6,337,298, 1/2002, Ebner et al. (withdrawn)
Carr–Brion et al, "On–Stream analyzer using multi–attenuated total reflectance" J. Scientific Instruments, vol. [2]2(2), pp. 155 156 (1969).*

(List continued on next page.)

*Primary Examiner*—Mukund J. Shah
*Assistant Examiner*—Zachary C. Tucker
(74) *Attorney, Agent, or Firm*—Senniger, Powers, Leavitt & Roedel; Joseph A. Schaper

(57) ABSTRACT

The present invention is directed to an analytical method for measuring the concentration of an N-(phosphonomethyl) iminodiacetic acid ("NPMIDA") substrate, an N-(phosphonomethyl)glycine product, formaldehyde, formic acid, N-methyl-N-(phosphonomethyl)glycine ("NMG"), N-methyl-aminomethylphosphonic acid (MAMPA) or aminomethylphosphonic acid ("AMPA")) in an aqueous mixture thereof, using infrared spectroscopy. The present invention is also directed to a process for oxidizing an N-(phosphonomethyl)iminodiacetic acid substrate to form a N-(phosphonomethyl)glycine product, and as part of the process, measuring the concentration of at least one reactant, product or byproduct of the oxidation reaction using the analytical method of the present invention and controlling the oxidation process in response to the measurement taken.

54 Claims, 18 Drawing Sheets

Formaldehyde Spectra

U.S. PATENT DOCUMENTS

| | | | |
|---|---|---|---|
| 5,889,683 | A | 3/1999 | Ismail et al. |
| 5,900,634 | A | 5/1999 | Soloman |
| 6,049,762 | A | 4/2000 | Ganz et al. |
| 6,096,553 | A | 8/2000 | Heald et al. |
| 6,117,820 | A | 9/2000 | Cutler et al. |

OTHER PUBLICATIONS

Riva et al, "Dossaggio Di Miscele Di Acidi Carbossilica Mediante Spettrofotometria Infrarossa in Riflettanza Totale Attenuatta" Industria Conserve, vol. 50(2), pp. 106–108. (1975).*

Piccolo and Celano, "Modification of Infrared Spectra of the Herbicide Glyphosate Induced by pH Variation" J. Environ. Sci. Health, vol. B28(4), pp. 447–457 (1993).*

Barja and Dos Santos Afonso, "An ATR–FTIR Study of Glyphosate and Its Fe(III) Complex in Aqueous Solution" Environ. Sci. Technol., vol. 32, pp. 3331–3335 (1998).*

U.S. patent application Publication No. US 2002/0068836 A1 entitled "Reaction Systems for Making N–(Phosphonomethyl)Glycine Compounds", published Jun. 6, 2002, 134 pages.

International Search Report for Application No. PCT/US 02/15894 (MTC 6767.2), dated Oct. 7, 2002, 5 pages.

* cited by examiner

Formic Acid Spectra

GI Spectra

USE OF INFRARED SPECTROSCOPY FOR ON-LINE PROCESS CONTROL AND ENDPOINT DETECTION

REFERENCE TO RELATED APPLICATION

This application claims priority from U.S. provisional application Ser. No. 60/292,659, filed on May 22, 2001, the entire disclosure of which is incorporated herein by reference.

FIELD OF THE INVENTION

The present invention relates generally to a method of measuring the concentration of at least one reactant, product or byproduct of liquid-phase oxidation processes for making N-(phosphonomethyl)glycine (also known in the agricultural chemical industry as "glyphosate") and related compounds and a method for controlling the oxidation process based on the concentration measured. More particularly, this invention relates to a method for quantitatively analyzing aqueous mixtures comprising an N-(phosphonomethyl) iminodiacetic acid ("NPMIDA") substrate (i.e., N-(phosphonomethyl)iminodiacetic acid, a salt of N-(phosphonomethyl)iminodiacetic acid, or an ester of N-(phosphonomethyl)iminodiacetic acid), an N-(phosphonomethyl)glycine product (i.e., N-(phosphonomethyl)glycine, a salt of N-(phosphonomethyl)glycine, or an ester of N-(phosphonomethyl)glycine), formaldehyde, formic acid, N-methyl-N-(phosphonomethyl)glycine ("NMG"), aminomethylphosphonic acid (AMPA), N-methyl-aminomethylphosphonic acid (MAMPA) or aminomethylphosphonic acid ("AMPA")) using infrared spectroscopy and more particularly Fourier transform infrared (FTIR) spectroscopy. The present invention also relates to a method for using the analytical method to control a liquid process wherein an N-(phosphonomethyl)iminodiacetic acid substrate is oxidized to form a N-(phosphonomethyl)glycine product.

BACKGROUND OF THE INVENTION

N-(phosphonomethyl)glycine is described by Franz in U.S. Pat. No. 3,799,758. N-(phosphonomethyl)glycine and its salts are conveniently applied as a post-emergent herbicide in an aqueous formulation. It is a highly effective and commercially important broad-spectrum herbicide useful in killing or controlling the growth of a wide variety of plants, including germinating seeds, emerging seedlings, maturing and established woody and herbaceous vegetation, and aquatic plants.

One of the more widely accepted methods of making N-(phosphonomethyl)glycine compounds comprises oxidatively cleaving a carboxymethyl substituent from a N-(phosphonomethyl)iminodiacetic acid substrate. Over the years, a wide variety of methods have been disclosed for conducting this oxidation. See generally, Franz, et al., *Glyphosate: A Unique Global Herbicide* (ACS Monograph 189, 1997) at pp. 233–62 (and references cited therein); Franz (U.S. Pat. No. 3,950,402); Hershman (U.S. Pat. No. 3,969,398); Chou (U.S. Pat. No. 4,624,937); Chou (U.S. Pat. No. 4,696,772); Ramon et al. (U.S. Pat. No. 5,179,228); Felthouse (U.S. Pat. No. 4,582,650); Siebenhaar et al. (PCT/EP99/04587); and Ebner et al. (PCT/US99/03402). Generally, these processes produce suitable yields, however they also produce formaldehyde (HCHO) as a byproduct. Formic acid ($HCO_2H$) also tends to be formed by the oxidation of the formaldehyde byproduct. These byproducts are undesirable because they tend to react with the N-(phosphonomethyl)glycine product to produce unwanted by-products (mainly N-methyl-N-(phosphonomethyl) glycine ("NMG") and N-formyl-N(phosphonomethyl) glycine ("NFG")) which reduce the N-(phosphonomethyl) glycine product yield. In addition, the formaldehyde by-product itself is undesirable because of its potential toxicity.

The oxidation reaction may be practiced using a wide range of temperatures, and at pressures ranging from sub-atmospheric to super-atmospheric. Moreover, the precise conditions and reaction rate under which the oxidation process is conducted affects the concentration of not only the un-reacted N-(phosphonomethyl)iminodiacetic acid substrate and the N-(phosphonomethyl)glycine in the final reaction mixture, but also the concentrations of undesirable byproducts (e.g., formaldehyde, formic acid, N-methyl-N-(phosphonomethyl)glycine ("NMG"), and aminomethylphosphonic acid ("AMPA")). Although the analysis of these mixtures may be performed by periodically sampling the reaction mixture and analyzing the sample using high pressure liquid chromatography, a need exists for an analytical method which allows for on-line analysis to provide real-time concentration data to allow for real-time monitoring and control of the oxidation process.

SUMMARY OF THE INVENTION

Among the objects of the present invention, therefore is the provision of an analytical method for determining the concentration of an analyte of an aqueous mixture comprising N-(phosphonomethyl)iminodiacetic acid, a salt of N-(phosphonomethyl)iminodiacetic acid, an ester of N-(phosphonomethyl)iminodiacetic acid), N-(phosphonomethyl)glycine, a salt of N-(phosphonomethyl)glycine, an ester of N-(phosphonomethyl)glycine), formaldehyde, formic acid, N-methyl-N-(phosphonomethyl)glycine, N-methyl-aminomethylphosphonic acid, aminomethylphosphonic acid, or mixtures thereof; the provision of an analytical method for determining the concentration of an analyte in said aqueous mixture to provide real time or substantially real time measurements of a process for oxidizing an N-(phosphonomethyl)iminodiacetic acid substrate to form a N-(phosphonomethyl)glycine product; and the provision of a process for oxidizing an N-(phosphonomethyl) iminodiacetic acid substrate to form a N-(phosphonomethyl) glycine product wherein as part of the process, measuring the concentration of an analytic using the analytical method of the present invention, and controlling the oxidation process in response to the measurement.

Briefly therefore, the present invention is directed to a method for determining the concentration of an analyte of an aqueous mixture comprising N-(phosphonomethyl) iminodiacetic acid, a salt of N-(phosphonomethyl) iminodiacetic acid, an ester of N-(phosphonomethyl) iminodiacetic acid), N-(phosphonomethyl)glycine, a salt of N-(phosphonomethyl)glycine, an ester of N-(phosphonomethyl)glycine), formaldehyde, formic acid, N-methyl-N-(phosphonomethyl)glycine, N-methyl-aminomethylphosphonic acid, aminomethylphosphonic acid, or mixtures thereof. The method includes measuring an electromagnetic absorbance spectrum for the aqueous mixture over an infrared wavenumber range of from about 200 $cm^{-1}$ to about 5000 $cm^{-1}$ and using data from the electromagnetic absorbance spectrum in a chemometric model to determine the concentration of the analyte in the aqueous mixture, the chemometric model being a mathematical relationship between the concentration of the analyte in the aqueous mixture as a function of the electromaganetic absorbance spectrum of the mixture.

The present invention is further directed to a process for the preparation of an N-(phosphonomethyl)glycine product selected from the group consisting of N-(phosphonomethyl) glycine, a salt thereof or an ester thereof by oxidation of an N-(phosphonomethyl)iminodiacetic acid substrate selected from the group consisting of N-(phosphonomethyl) iminodiacetic acid, a salt thereof or an ester thereof. The process includes contacting said substrate with an oxygen containing gas in the presence of a catalyst for the reaction, measuring the concentration in real time or substantially real time of an analyte in the reaction mixture, the analyte being selected from a group consisting of N-(phosphonomethyl) iminodiacetic acid, a salt of N-(phosphonomethyl) iminodiacetic acid, an ester of N-(phosphonomethyl) iminodiacetic acid), N-(phosphonomethyl)glycine, a salt of N-(phosphonomethyl)glycine, an ester of N-(phosphonomethyl)glycine), formaldehyde, formic acid, N-methyl-N-(phosphonomethyl)glycine, N-methyl-aminomethylphosphonic acid, or aminomethylphosphonic acid and controlling the conversion of N-(phosphonomethyl)iminodiacetic acid substrate to affect the concentration of the measured analyte in the reaction mixture.

Other objects and features of this invention will be in part apparent and in part pointed out hereinafter.

DETAILED DESCRIPTION OF THE PREFERRED EMBODIMENTS

Figure 1:
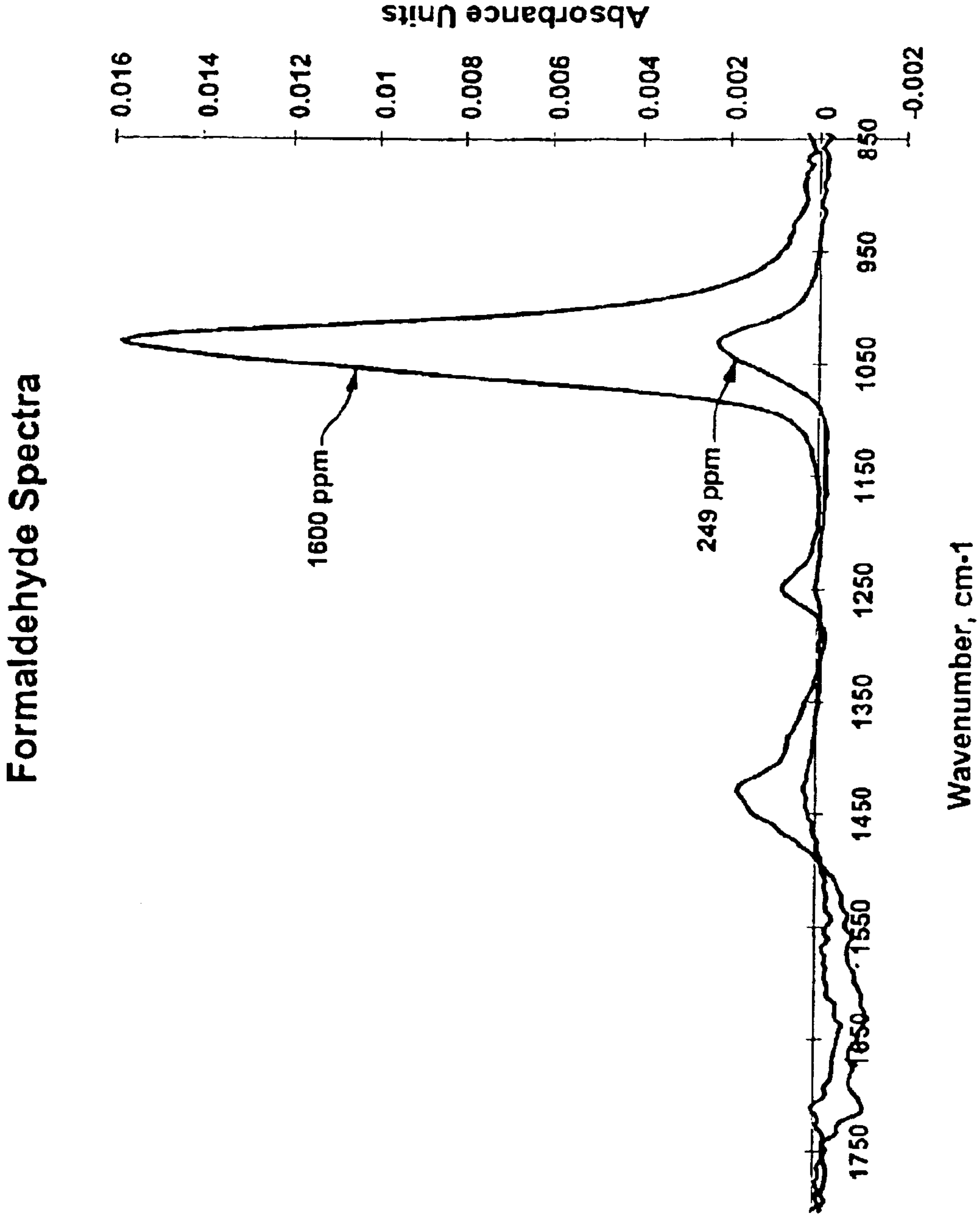
FIG. 1 shows example absorbance spectra is for samples having a known formaldehyde concentration.
Figure 2:
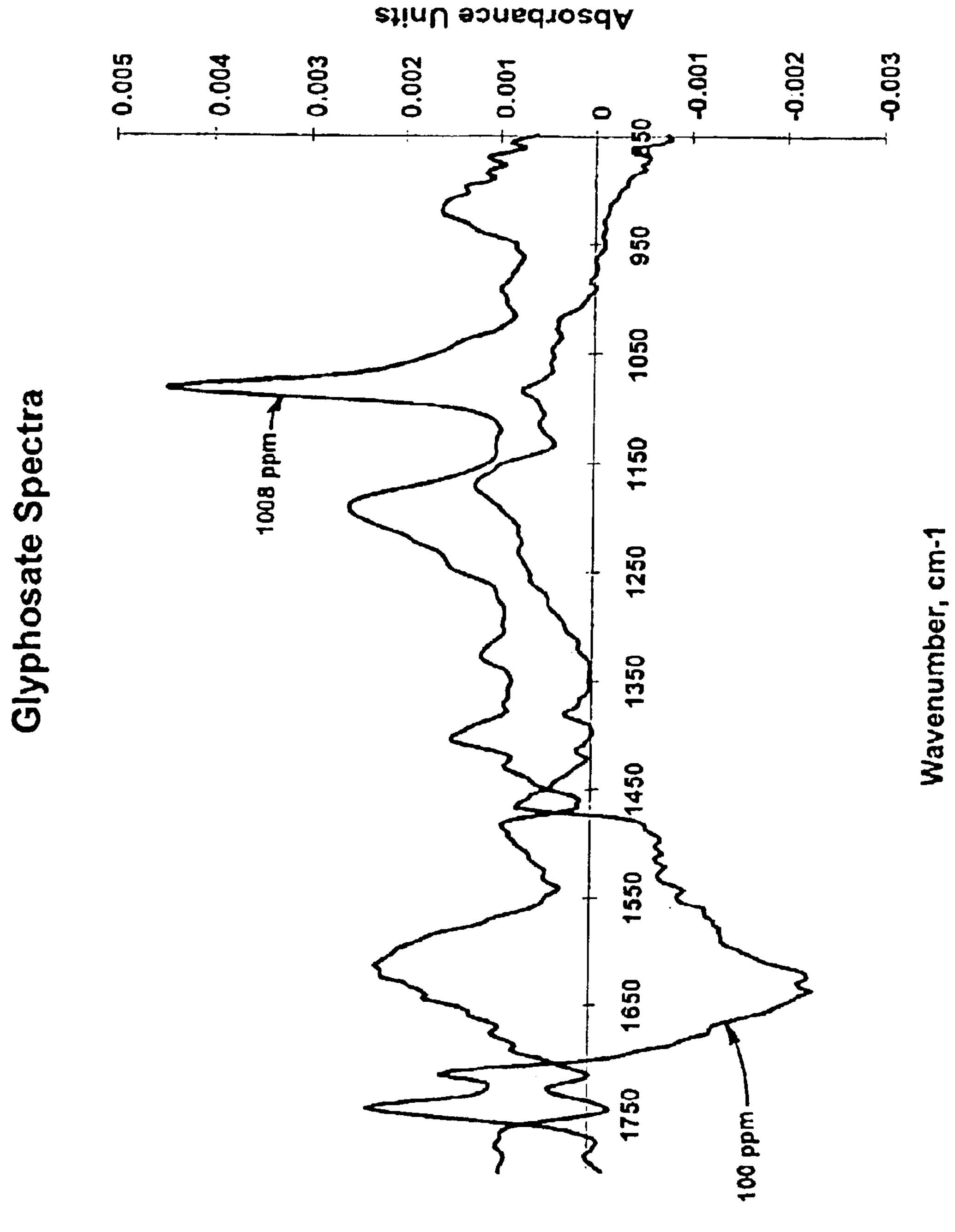
FIG. 2 shows example absorbance spectra is for samples having a known glyphosate concentration.
Figure 3:
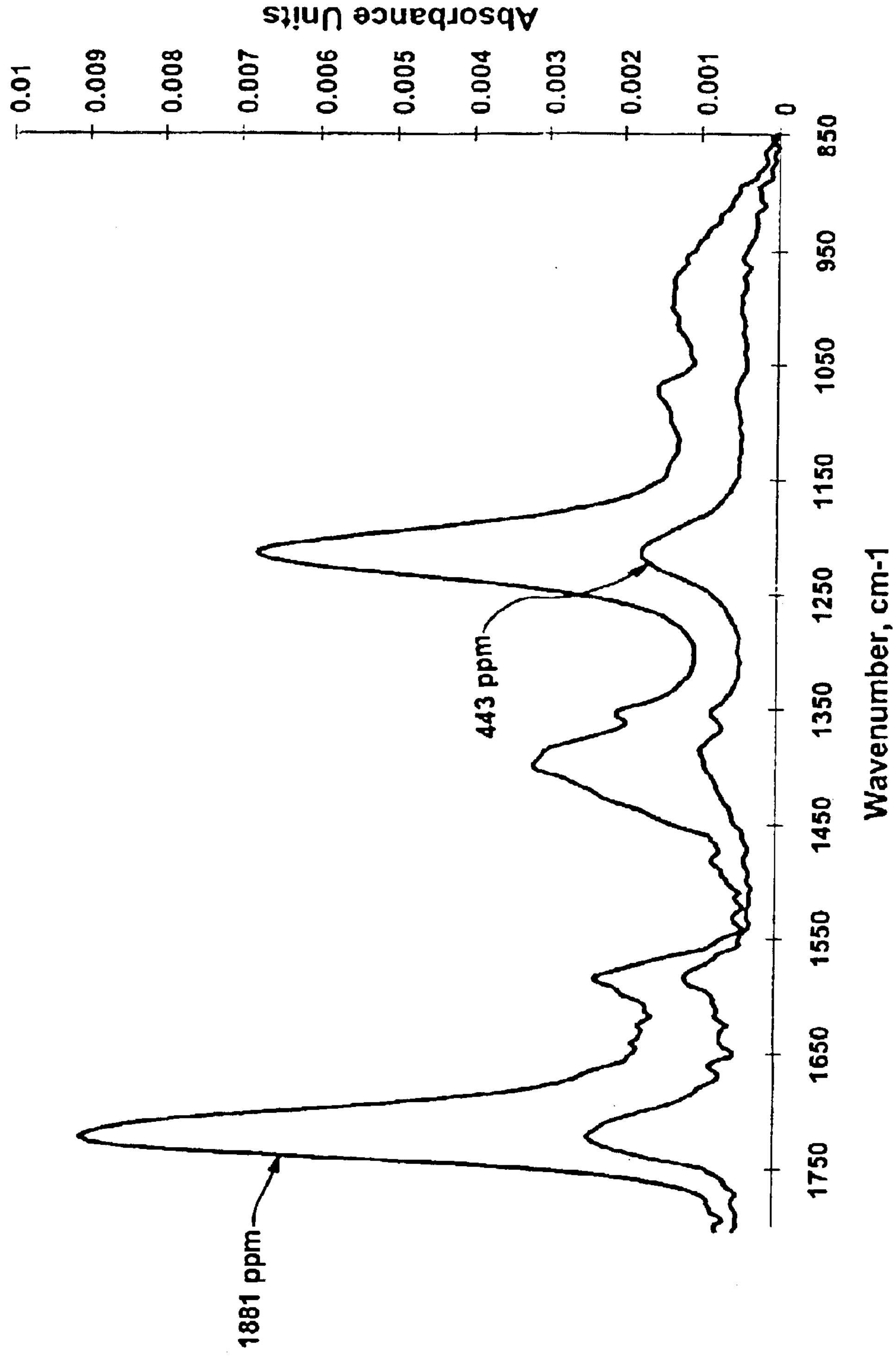
FIG. 3 shows example absorbance spectra is for samples having a known formic acid concentration.
Figure 4:
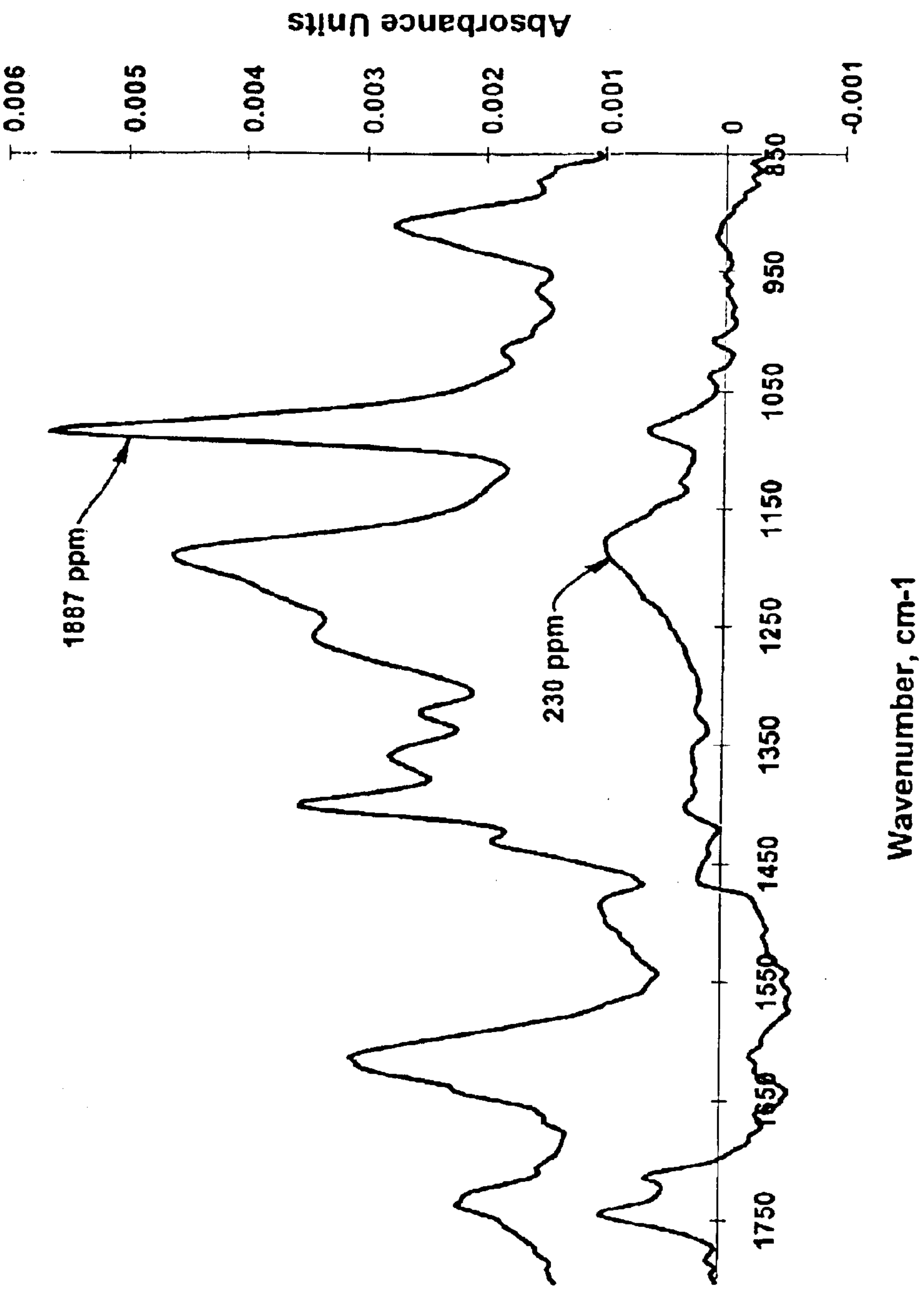
FIG. 4 shows example absorbance spectra is for samples having a known glyphosate intermediate (GI) concentration.

In general, the present invention relates to an analytical method for measuring the concentration of an N-(phosphonomethyl)iminodiacetic acid ("NPMIDA") substrate (i.e., N-(phosphonomethyl)iminodiacetic acid, a salt of N-(phosphonomethyl)iminodiacetic acid, or an ester of N-(phosphonomethyl)iminodiacetic acid), an N-(phosphonomethyl)glycine product (i.e., N-(phosphonomethyl)glycine, a salt of N-(phosphonomethyl)glycine, or an ester of N-(phosphonomethyl)glycine), formaldehyde, formic acid, N-methyl-N-(phosphonomethyl)glycine ("NMG"), N-methyl-aminomethylphosphonic acid (MAMPA) or aminomethylphosphonic acid ("AMPA")) in an aqueous mixture comprising an N-(phosphonomethyl)iminodiacetic acid ("NPMIDA") substrate, an N-(phosphonomethyl)glycine product, formaldehyde, formic acid, N-methyl-N-(phosphonomethyl)glycine ("NMG"), N-methyl-aminomethylphosphonic acid (MAMPA) aminomethylphosphonic acid ("AMPA")) or mixtures thereof, using infrared spectroscopy. The present invention also relates to a process comprising oxidizing an N-(phosphonomethyl) iminodiacetic acid substrate to form a N-(phosphonomethyl) glycine product, and as part of the process, measuring the concentration of at least one reactant, product or byproduct of the oxidation reaction using the analytical method of the present invention and controlling the oxidation process in response to the measurement taken.

I. Analytical Method

Spectrometric instruments are frequently used for a variety of applications associated with analyses of materials. A spectrum is generated in interaction with a sample material to effect a spectral beam that is characteristic of the sample and impinged on a photodetector. Typically spectrometric instruments include a computer that receives spectral data from the detector to generate and compare spectral information associated with the sample material. The spectrum may be generated, for example, by a dispersion element such as a prism or a holographic grating that spectrally disperses light passed by a sample or received from a plasma or other excitation source containing sample material. Another type of instrument incorporates a time varying optical interference system, in which an interference pattern of light is produced and passed through a sample material and is modified according to the absorption characteristics of the sample. In such an instrument Fourier transform computations are applied to the detector signals to generate the spectral data. The Fourier transform instrument is most commonly operated in the infrared range, in which case it is known as a Fourier transform infrared (FTIR) instrument or spectrometer. Infrared refers to the region of the electromagnetic spectrum including wavelengths ranging from about 2 to about 50 microns, i.e., wave numbers ranging from about 200 to 5000 $cm^{-1}$ with the wave number being the reciprocal of wavelength and proportional to frequency.

Conventional FTIR spectrometers are taught in textbooks such as "Fourier Transform Infrared Spectrometry" by P. R. Griffiths and J. A. de Haseth (Wiley, 1986). In FTIR spectrometers, an interference pattern of light is produced with a Michaelson or similar interferometer comprising a beam splitter which is a partial reflector that splits white light into two beams. These beams are reflected back and recombined at the beam splitter. The path length of one of the beams is varied with time to produce a time-varied interference pattern. This light pattern is directed through an angle-selecting aperture and thence through a sample material that modifies the interference pattern of the beam. A detector then measures the intensity or amplitude of the modified beam for each wavenumber producing an interferogram i.e., intensity as a function of wavenumber. Alternatively, a number of scans may be performed generating an interferogram for each scan. Fourier transform computations transform the interferogram into a spectrum in the form of transmittance verses wavenumber, or more preferably absorbance verses wavenumber. If multiple scans are to be performed for each measurement, the Fourier transform additionally performs an averaging function such that numerous interferograms are transformed into a single spectrum.

In one application, FTIR spectroscopy is used to qualitatively or quantitatively determining specific information about the identity and quantity of a chemical species, or analyte, within a sample. That is, FTIR spectroscopy may be used to measure the absorbance by a sample of a continuum of wavenumbers within the infrared spectral region ranging from about 200 to about 5000 $cm^{-1}$. The absorbance spectrum may then be used to determine presence and concentration of an analyte based on the wavenumber or range of wavenumbers absorbed and the magnitude of the absorbance of particular spectral regions. Stated differently, a chemical species will absorb radiation in particular spectral regions creating a characteristic spectral profile according to the chemical structure of the species. A chemometric model determined for an analyte calculates the concentration of that analyte as a function of the magnitude of the absorbance in these spectral regions. The chemometric model is determined using multivariate mathematical correlation techniques to develop the model based on spectral measurements of a number of standards wherein the concentration of the analyte being modeled is known.

In a preferred embodiment of the present invention in-line Fourier transform infrared (FTIR) spectroscopy is used to quantitatively measure one or more of N-(phosphonomethyl)iminodiacetic acid ("NPMIDA") substrate, an N-(phosphonomethyl)glycine product, formaldehyde, formic acid, N-methyl-N-(phosphonomethyl)glycine ("NMG"), N-methyl-aminomethylphosphonic acid ("MAMPA") or aminomethylphosphonic acid ("AMPA")) in aqueous mixtures thereof. More preferably, the present invention uses an internal reflectance FTIR method for "in-situ" measurement of the infrared spectrum absorbed by a reaction mixture. That is, the internal reflectance FTIR method allows for the reaction mixture to be measured in place by locating a sensor probe in, on or in proximity to a process line or reaction vessel so that it is immersed in the reaction mixture or positioned on a direct or reflected line of site to the reaction mixture thus allowing the reaction mixture to be directly scanned in substantially real time without removing a sample of the mixture from the vessel or process line in which it is contained. Advantageously in-situ measurements provide real time or substantially real time measurements of the reaction mixture.

In general, internal reflectance relates to a process wherein an infrared light beam is modulated using an interferometer, and the modulated beam is reflected off a sample and returned to a detector wherein the spectral regions absorbed as well as the intensity of the absorbance within those regions is determined. One technique for practicing the internal reflectance method is attenuated total reflectance (ATR) spectrometry which measures the absorbance in a thin layer of the sample in contact with the sampling surface of a sensor device. That is, a sensor probe is placed in direct contact with the sample. A modulated infrared beam is transmitted from the FTIR spectrometer to the sensor probe wherein the beam is transmitted through a sampling surface on the probe such that the beam penetrates into a thin layer of the sample in contact with the sampling surface of the probe and is reflected back into the sensor probe. Significantly, the beam is modified by the sample due to the absorbance characteristics of the sample. The modified beam is then optically transmitted to the FTIR spectrometer's detector. Depending on the ATR probe selected, i.e., the optical characteristics and geometry of the sampling surface, the modulated infrared beam may reflect off of both the sample layer and the sampling surface a number of times before finally returning back into the sensor probe, providing additional data to the detector. Thus, ATR probes are typically described by the number of reflections that occur through the sample layer. Preferably, the ATR probe utilizes at least about 3, more preferably at least about 6 and still more preferably at least about 9 reflections or greater.

Since the sampling surface is the primary optical element in the sensor probe, i.e., the infrared beam is transmitted through the sampling surface to the sample, the sampling surface preferably has optical characteristics which minimize interference within the spectral regions of the infrared beam and in particular within the spectral regions characteristic of the analyte being measured. In addition, because the ATR probes are typically inserted directly into the process streams or reactor vessels to allow in-situ measurement of the reaction mixtures, it is preferred that the sampling surface of the probe be constructed of a material that is relatively inert with regard to the reaction mixture.

The reaction mixtures described herein generally have a low pH creating a corrosive environment. Additionally, the reaction mixtures may contain solid catalyst and potentially undissolved product which may adhere to or abrade the sampling surface. Therefore, it is preferred that the sampling surface of the probe be resistant to mechanical abrasion and have a relatively low coefficient of friction to prevent the adherence of particles. Diamond surfaces typically have a characteristic absorption band located from about 1900 to about 2200 $cm^{-1}$ which does not interfere with the characteristic absorption profiles of the analytes in the reaction mixture and therefore have desirable optical characteristics for use in measuring the spectral absorption of the reaction mixture. Moreover, diamond provides resistance to chemicals and abrasion and has a low coefficient of friction and therefore can be placed directly in the reaction mixture without resulting in significant damage to the sampling surface.

Diamonds have a low coefficient of expansion, which allows probes having a diamond sampling surface to be used in conditions wherein the temperature is no greater than about 200° C. and the pressure is no greater than about 150 psi. Advantageously, the reaction temperatures and pressure conditions for the oxidation process are within the typical operating ranges of ATR probes having a diamond optical surface.

Preferably, therefore the sampling surface of the ATR probe is comprised of diamond. ATR probes comprising a diamond sampling surface may further comprise an additional optical element which acts both as a support for the diamond, and for transmitting and focusing the modulated infrared beam to and from the diamond sampling surface. Since the second optical element is not in contact with the reaction mixture, it is less important that the second optical element have the corrosion and abrasion resistance as the sampling surface. Zinc selenide crystals have similar optical qualities as diamond at a substantially reduced cost. Accordingly, zinc selenide may be used as an additional optical element.

Finally, the sampling surface of the ATR probes may be concave, convex or have a relatively flat surface curvature. Preferably, the sampling surface of the ATR probe is relatively flat. Without being held to a particular theory, it is believed that sampling surface having a significant degree of curvature tend to promote the adherence of particulates such as catalyst or undissolved product to the sampling surface thereby interfering with the sensor.

ATR probes having the characteristics described above, i.e., a relatively flat diamond sampling surface are commercially available, for example, from Axiom Analytical, Inc. (Irvine, Calif.). In a preferred embodiment, a 9 reflection, diamond-composite sensor probe having a relatively flat diamond sampling surface, such as a DiComp™ Sentinal™ ATR diamond-composite sensor probe which is commercially available from ASI Applied Systems (Annapolis, Md.), is used.

Although a flat sampling surface reduces the potential for solids to adhere to the sampling surface, some applications may additionally require that the surface be periodically cleaned to prevent the buildup of solids on the sampling surface. Accordingly, an ultrasonic cleaner may be used to flush the sampling surface of the probe. If an ultrasonic cleaner is used, the sampling surface may be cleaned using ultrasonic pulses of at least about 5 seconds, more preferably at least about 10 seconds, still more preferably at least about 15 seconds and still more preferably at least about 25 seconds with the pulses occurring at intervals ranging from about 100 to about 300 seconds, more preferably from about 125 to about 175 seconds still more preferably from about 140 to about 150 seconds. The precise duration and frequency of ultrasonic pulses may vary depending on the particular location of the probe and the qualities of the mixture being sampled. Accordingly, the duration and frequency of the ultrasonic pulses may be varied without departing from the scope of the present invention.

The FTIR spectrometer detects the intensity or amplitude of the modified beam across the infrared region and transforms the data into an absorbance spectrum i.e., absorbance vs. wavenumber. FTIR spectrometers typically use two types of detectors, a mercury cadmium telluride (MCT) detector or a deuterated triglycine sulfate (DTGS) detector. Although MCT detectors tend to be faster than DTGS detectors and have a high sensitivity, MCT detectors typically require liquid nitrogen cooling. Therefore, it may be preferred to use a DTGS detector which does not require liquid nitrogen cooling. Either type of detector may be used without departing from the scope of the present invention.

According to the present invention, the reaction mixture is sampled over a spectral range of wavelengths from about 200 to 5000 $cm^{-1}$, more preferably from about 650 to about 4000 $cm^{-}$. The infrared spectrum is a continuous spectrum, however for analytical reasons, discrete wavenumbers or groups of wavenumbers are typically measured. The wavenumber resolution, i.e., the range of wavenumbers that are grouped together for each discrete measurement may be increased or decreased to affect the signal to noise ratio of the FTIR spectrometer. That is, as the numerical value of the wavenumber resolution is decreased, more measurements are taken across the spectrum and the resolution of the spectrum increases. However, increases in the wavenumber resolution also typically results in a corresponding increase in the level of “noise”. Generally, FTIR spectroscopy methods use wavenumber resolutions having a numerical value of 2, 4, 8 or 16, i.e., sample data are collected over discrete ranges of 2, 4, 8 or 16 wavenumbers with the resolution being inversely proportional to the numerical value of the wavenumber resolution. Typically, a wavenumber resolution of 8 appears to provide a spectrum with a fairly good resolution while minimizing the amount of “noise.” Changes in the wavenumber resolution may be made, however, without departing from the scope of the present invention.

Additionally, FTIR spectroscopy generally utilizes a number of scans providing additional interferometric data i.e., intensity verses wavenumber data used in the Fourier transform to produce the spectral data i.e., absorbance verses wavenumber. If the number of scans is set at 180, for example, the spectrometer will scan the entire wavelength range specified 180 times and produce 180 interferograms, or 180 intensity measurements per wavenumber, or more precisely, per wavenumber grouping as determined by the wavenumber resolution. Fourier transforms then combine the intensity data and convert the 180 interferograms into a single absorbance spectrum. The number of spectra i.e., scans can also affect the signal to noise ratio. Generally about 180 scans may be sampled with a new spectrum measurement being generated about every 145 seconds. More preferably, the number of scans is at least about 360, producing a new measurement every 5 minutes or greater in an effort to improve the signal to noise ratio.

Preferably, the number of scans performed is such that the frequency in which new spectrum measurements are taken is less than about the residence time of the oxidation reaction zone affecting the concentration being measured. That is, the oxidation process may utilize one, two or more reaction zones for converting the N-(phosphonomethyl) iminodiacetic acid (“NPMIDA”) substrate to N-(phosphonomethyl)glycine product. Each reaction zone has a corresponding residence time in which the reaction takes place. In addition, if these reaction zones are placed in series, there will additionally be an overall residence time for the reaction system comprising the summation of the residence times for each reaction zone. The residence time considered for determining the sample frequency depends on whether an analyte is being measured to monitor the progress of the oxidation reaction in a particular reaction zone, or the progress of the overall reaction system.

Preferably at least one, more preferably at least two, and still more preferably at least three measurements are taken within a time period of no greater than the residence time for the oxidation reaction zone being monitored. Typically, the residence time for a particular reaction zone may vary from about 3 to about 120 minutes, more preferably from about 5 to about 90 minutes, still more preferably from about 5 to about 60 minutes, and still even more preferably from about 15 to about 60 minutes. The residence time for a particular reaction system may vary depending on the total throughput and the quantity of the reaction mixture in the reactor without departing from the scope of the present invention.

A single analyte will produce a spectrum having an absorbance profile characteristic of that analyte. That is, the spectrum contains absorbance features that may be associated with the analyte. Accordingly, the concentration of the analyte may be determined using a mathematical model representing the relationship between the concentration of the analyte and the absorbance profile. The mathematical model may be developed by measuring the spectrum for a number of standard samples having known concentrations and mathematically correlating the concentration as a function of the absorbance profile using a number of correlation methods. Unfortunately, the characteristic spectrum for a mixture of analytes such as the reaction mixture is more complex in that the characteristic absorbance spectrum for the various analytes are broad and overlap significantly. This overlap precludes the use of simple univariate correlation methods for quantitation of the analytes in a reaction mixture. This problem may be overcome by applying more powerful multivariate mathematical correlation techniques to the analysis of the spectral data. These multivariate mathematical techniques when applied to process chemical analysis are collectively referred to as chemometrics. This technique uses complex mathematics such as matrix vector algebra and statistics to extract quantitative information (e.g., concentrations) from highly convoluted or statistically confounded data such as the spectrum obtained from a mixture of analytes to develop a mathematical model, also called a chemometric model representing the quantitative information as a function of the spectrum. A number of multivariate mathematical techniques have been developed such as; K-Nearest Neighbors analysis (KNN), Hierarchical Cluster Analysis (HCA), Principal Component Analysis (PCA), Partial Least Squares (PLS) analysis, and Principal Component Regression (PCR) analysis. Commercially available software packages are capable of performing many of the multivariate mathematical correlation techniques listed above. In fact, at least one commercially available software package called "Pirouette" (which can be obtained from Infometrics, Inc., P.O. Box 1528 Woodinville, Wash. 98072) is capable of perform all of the correlation techniques listed above.

Commercially available FTIR spectrometers often include chemometric analysis software. In particular, PLS and PCR are typically used for determining a chemometric model, and applying it to a FTIR spectral measurement to calculate a property of the sample measured. Of these two, PLS is most commonly applied to FTIR spectral data because it generally provides the most accurate chemometric models. PLS allows each analyte to be modeled separately, and only requires knowledge of the particular analyte being modeled. That is, it does not require that the concentration of each absorbing analyte be known as long as each absorbing analyte is represented in the standards used for developing the chemometric model. Advantageously, the standards can be taken directly from the process and need not be separately prepared, thus allowing consideration of the impurity profile of the reaction mixture when determining the chemometric model for each analyte to be measured. However, it should be noted that the absorbance of the spectral regions is generally nonlinear with respect to concentrations. Thus, the chemometric models correlating the concentration and the absorbance spectrum should be developed over particular ranges of concentration for the individual analytes of the reaction mixture. That is, the standards used in the chemometric analysis should be representative of the matrix of concentrations for each analyte in the mixture.

In general, therefore, a number of standards are analyzed using the FTIR Spectrometer to measure the spectrum for each standard. The concentration of a particular analyte can then be mathematically modeled as a function of the spectra obtained i.e., an algorithm is developed that correlates the concentration and the spectrum. Although any of the multivariate mathematical calibration techniques may be used, a preferred embodiment uses the PLS method to model the spectra as a function of concentration. The number of standards used is preferably at least about 10 and more preferably at least about 20. In general, the accuracy of the model increases with increases in the number of standards used to generate the model. Therefore, the number of standards used to generate the model may be as high as 50 or greater. Such standards may be prepared mixtures, or alternatively, may be samples of the particular process mixture to be analyzed. However, as stated earlier, it is preferred that the process mixture is used such that the impurity profile is considered in the PLS analysis when generating the chemometric model. The concentration of the analyte being modeled in each standard may be measured off-line using standard analytical techniques such as high pressure liquid chromatography (HPLC). Accordingly, chemometric models may be generated using a partial least squares regression analysis for spectra obtained from reaction mixtures from either a batch or a continuous oxidation process based on-line spectral measurements and off-line HPLC concentration measurements.

As stated earlier, the FTIR scans the reaction mixture over a spectral range of wavelengths from about 200 to 5000 $cm^{-1}$ and more preferably from about 650 to about 4000 $cm^{-1}$. Although the entire spectral region scanned may be used in the PLS analysis, generally, the spectral region considered in the PLS analysis is preferably from about 800 to about 1800 $cm^{-1}$ when modeling the N-(phosphonomethyl)iminodiacetic acid ("NPMIDA") substrate, N-(phosphonomethyl)glycine product, formaldehyde or formic acid analytes. More preferably, however one or more spectral regions selected from the total spectrum are considered in the PLS analysis, with the regions being selected based on the analyte to be measured. For example, spectral regions to be considered in the PLS analysis may be selected by identifying spectral regions of characteristic peaks for each analyte in a solute such as water. Preferably however, the spectral region used in the PLS analysis to develop a chemometric model for N-(phosphonomethyl) iminodiacetic acid ("NPMIDA") is preferably from about 800 to about 1450 $cm^{-1}$, and more preferably from about 1065 to about 1400 $cm^{-1}$. The spectral region or regions used in the PLS analysis to develop a chemometric model for N-(phosphonomethyl)glycine in the reaction mixture are preferably from about 800 to about 1450 $cm^{-1}$ and more preferably both the region from about 865 to about 945 $cm^{-1}$ and the region from about 1280 to about 1460 $cm^{-1}$. The spectral region used in the PLS analysis to develop a chemometric model for formaldehyde is from about 800 to about 1450 $cm^{-1}$, more preferably from about 945 to about 1150 $cm^{-1}$, still more preferably from about 945 to about 1115 $cm^{-1}$ and still more preferably from about 1000 to about 1075 $cm^{-1}$. Finally, spectral region or regions used in the PLS analysis to develop a chemometric model for formic acid is from about 800 to about 1450 $cm^{-1}$, more preferably the region(s) from about 1150 to about 1300 $cm^{-1}$ and/or from about 1650 to about 1800 $cm^{-1}$. While the preferred spectral regions for formic acid provide reasonable accuracy at higher concentrations of formic acid, i.e., around from about 2,000 to about 5,000 ppm formic acid, the accuracy of the model decreased significantly at lower concentrations, i.e., less than about 1,000 ppm or even less than about 600 ppm. Significantly, a strong absorption band exists within the formic acid spectral region at around 1721 $cm^{-1}$. This band is close to the 1600 $cm^{-1}$ water region which, for aqueous mixtures, is subtracted out as a background and thus can be inconsistent and difficult to quantify. Thus, to minimize the effects of the water subtraction, the preferred spectral region used in the PLS analysis to develop a chemometric model for low concentrations of formic acid is preferably from about 1710 to about 1790 $cm^{-1}$. Surprisingly, by avoiding the spectral region which overlaps the water region, the present invention provides quantitative measurement of formic acid at concentrations less than about 1,000 ppm, less that about 600 ppm and even less than about 300 ppm.

Using the PLS analysis techniques therefore, chemometric models used to determine the concentration of N-(phosphonomethyl)iminodiacetic acid ("NPMIDA"), N-(phosphonomethyl)glycine, formaldehyde, and/or formic acid as a function of the absorption spectrum may be developed and used in combination with the FTIR spectrometer to provide real-time concentration data for process mixtures from either a batch or a continuous process thus allowing for improved studies of the reaction kinetics, improved reaction control, and in the case of the batch processes, a more accurate and timely reaction end point determination to be made.

For example, using the techniques described above, chemometric models have been developed using an FTIR spectrometer and a diamond-composite ATR probe such that the concentration of N-(phosphonomethyl)iminodiacetic acid ("NPMIDA") substrate in a reaction mixture may be measured over a range of concentrations of from about the detection limit, currently about 50 ppm, to about 4% with a PLS mean error of less than about 0.2% for a batch oxidation process and may be measured over a range of concentrations of from about 200 ppm to about 4,500 ppm with a mean error of about 200 ppm for a continuous oxidation process. The concentration of N-(phosphonomethyl)glycine product in a reaction mixture may be measured over a range of concentrations of from about 5% to about 10% with a mean error of less than about 0.2% for batch processes and may be measured over a range of concentrations of from about 4% to about 8% with a mean error of about less than about 0.2%, more preferably less than about 0.07% for the continuous process. The concentration of formaldehyde in a reaction mixture may be measured over a range of concentrations of from about 130 ppm to about 6,000 ppm with a mean error of less than about 150 ppm for batch processes and may be measured over a range of concentrations of from about 250 ppm to about 4,500 ppm with a mean error of about less than about 55 ppm and even over a range of concentrations of from about 100 ppm to about 400 ppm with a mean error of less than about 50 ppm and preferably less than about 30 ppm for the continuous process. Finally, the concentration of formic acid may be measured over a range of concentrations of from about 0.3% to about 1.3% with a mean error of less than about 0.03%, preferably less than about 0.02% for batch processes and may be measured over a range of from about 0.1% to about 0.4% with a mean error of about less than about 0.02%, more preferably less than about 0.01% for the continuous process.

II. Process Control

In general, the analytical method described above may be used to measure the progress of the oxidation of an N-(phosphonomethyl)iminodiacetic acid substrate selected from the group consisting of N-(phosphonomethyl) iminodiacetic acid, a salt thereof or an ester thereof to form an N-(phosphonomethyl)glycine product selected from the group consisting of N-(phosphonomethyl)glycine, a salt thereof or an ester thereof by contacting the substrate with an oxygen containing gas in the presence of a catalyst for the reaction.

The oxidation reaction may be practiced using a wide range of temperatures, and at pressures ranging from sub-atmospheric to super-atmospheric. Moreover, the precise conditions and reaction rate under which the oxidation process is conducted affects the concentration of not only the un-reacted N-(phosphonomethyl)iminodiacetic acid substrate and the N-(phosphonomethyl)glycine in the final reaction mixture, but also the concentrations of undesirable byproducts (e.g., formaldehyde, formic acid, N-methyl-N-(phosphonomethyl)glycine ("NMG"), and aminomethylphosphonic acid ("AMPA")).

The analytical method described above may be used to measure the progress of reaction or condition of the reaction mixture substantially in real time by substantially real time analysis of the reaction mixture for one or more analytes selected from the group consisting of N-(phosphonomethyl) iminodiacetic acid ("NPMIDA") substrate (i.e., N-(phosphonomethyl)iminodiacetic acid, a salt of N-(phosphonomethyl)iminodiacetic acid, or an ester of N-(phosphonomethyl)iminodiacetic acid), an N-(phosphonomethyl)glycine product (i.e., N-(phosphonomethyl)glycine, a salt of N-(phosphonomethyl)glycine, or an ester of N-(phosphonomethyl)glycine), formaldehyde, formic acid, N-methyl-N-(phosphonomethyl)glycine ("NMG"), N-methyl-aminomethylphosphonic acid (MAMPA) or aminomethylphosphonic acid ("AMPA")) in an aqueous mixture comprising an N-(phosphonomethyl)iminodiacetic acid ("NPMIDA") substrate, an N-(phosphonomethyl)glycine product, formaldehyde, formic acid, N-methyl-N-(phosphonomethyl)glycine ("NMG"), N-methyl-aminomethylphosphonic acid (MAMPA) aminomethylphosphonic acid ("AMPA")) or mixtures thereof, using infrared spectroscopy. In response to the substantially real time measurement, one or more process effects may be controlled by adjusting or maintaining the value of one or more independent process variables affecting the rate of oxidation of the substrate, the rate of oxidation of formaldehyde, the rate of oxidation of formic acid, the rate of oxidation of N-(phosphonomethyl)glycine product to aminomethylphosphonic acid or salt or ester thereof. Independent process variables affecting the rate of oxidation of the substrate, the rate of oxidation of formaldehyde, the rate of oxidation of formic acid, the rate of oxidation of N-(phosphonomethyl) glycine product to aminomethylphosphonic acid (or salt or ester thereof) include but are not necessarily limited to: the rate of introduction of molecular oxygen into said continuous reaction zone, the rate of withdrawal of gas from said reaction zone, the oxygen partial pressure at a select location within said reaction zone or in contact with said liquid reaction medium, the temperature of said reaction mixture, the rate of introduction of said aqueous feed mixture to said reaction zone, the rate of withdrawal of said reaction mixture from said reaction zone, the amount of catalyst added to said reaction zone, the amount of catalyst removed from said reaction zone, the amount of a supplemental promoter added to the reaction zone and the intensity of agitation of the reaction mixture.

For example, the oxidation reaction may be carried out in a batch process. An internal reflectance sensor, preferably an ATR probe is inserted directly into the reactor, or alternatively is placed in-line with a recycle loop to enable in-situ real time or substantially real time measurements of the concentration of at least one of the analytes in the reaction mixture. The progress of the reaction can be determined by monitoring the decrease in the concentration of the substrate, for example, or alternatively by monitoring the increase in the concentration of the an N-(phosphonomethyl) glycine product, thus enabling real time or substantially real time determinations of the reaction endpoint. In addition, the data from the FTIR may be electronically communicated to a conventional process control apparatus. Preferably the process controller is configured such that in response to the data showing the end point of the reaction had been reached, the process controller instructs a control device such as a control valve to terminate the addition of the oxygen containing gas such that the oxidation reaction is terminated. It should be noted that the above example is for illustrative purposes only and in no way is intended to limit the manner in which the progress of the batch oxidation process or the condition of the reaction mixture therein is controlled in response to the analyte concentration measurement provided by the analytical method of the present invention.

Preferably, the oxidation reaction is a continuous oxidation process as described U.S. patent application Ser. No. 09/863,885, the entire contents of which are incorporated herein by reference. In a more preferred embodiment, the oxidation reaction is carried out using two oxidation reaction zones in series.

In one embodiment, the concentration of unreacted N-(phosphonomethyl)iminodiacetic acid substrate, N-(phosphonomethyl)glycine product and/or oxidation byproducts in the reaction mixture effluent are measured using the analytical method described above. In a particularly preferred embodiment of the present invention, the concentration of unreacted N-(phosphonomethyl) iminodiacetic acid substrate, N-(phosphonomethyl)glycine product and/or oxidation byproducts in the intermediate aqueous reaction mixture withdrawn from the first stirred tank reactor and/or in the final reaction mixture effluent withdrawn from the second stirred tank reactor may be measured using the analytical method described above. Based on these and other process measurements, control adjustments can be made, thus the conversion of the substrate and condition of the reaction mixture may be controlled by controlling the total oxygen feed to the continuous reactor system, i.e., both the stirred tank reactors and/or the apportionment of the total oxygen feed between the first and second stirred tank reactors and may be adjusted to beneficially affect the yield and quality of the N-(phosphonomethyl)glycine product. Alternatively, other variables may be controlled such as the partial pressure of oxygen at a select location within either or both reaction zones or in contact with the liquid reaction medium of each reaction zone, the rate of withdrawal of gas from either or both reaction zones, the temperature of the liquid reaction medium within the either or both reaction zones or exiting either or both reaction zones, the rate of withdrawal of reaction product from either or both reaction zones, the liquid level of reaction mixture in either or both reaction zones, the weight of reaction medium in either or both reaction zones, addition or removal of catalyst to the reaction system via either or both reaction zones, shifting the relative proportions of the total catalyst mass in either or both reaction zones as well as a catalyst holding tank, the addition of supplemental promoter to either or both reaction zones and the intensity of mixing in either or both reaction zones.

Moreover, in making adjustments of control variables in response to FTIR analysis, other process effects may be taken into account, e.g., the oxygen content of the gas withdrawn from the reaction zone(s), dissolved oxygen in the liquid medium in the reaction zone(s), the potential of an oxygen electrode or oxidation/reduction potential electrode, and the noble metal content of the liquid phase of the reaction mixture withdrawn from the reaction zone. By considering these together with current values for control variables and real time FTIR analysis of the concentrations of one or more analytes in the reaction mixture(s), one or more control variables may be adjusted to conform the process to established process constraints and/or to optimize economically significant outputs such as yield, conversion, selectivity, by-product content and process emissions. With the benefit of substantially real time analysis of reaction mixture composition, optimization can be determined either ad hoc based on known process performance relationships, or in accordance with protocols that have been established based on such relationships. As appropriate, material balance, energy balance, kinetic, mass transfer, heat transfer, thermal stability, catalyst deactivation profiles, and other conventional considerations can form the basis for establishing protocols. As may be convenient, such protocols may optionally be reduced to algorithms which can be programmed onto a processor. Assimilating additional information, including both control variables and performance measurements such as those described above, the processor may then determine optimum settings for one or more of the aforesaid independent variables in accordance with the protocol for obtaining a desired or optimal value for the concentration of one or more of the analytes with respect to an economic or process criterion selected from the group consisting of conversion of substrate, yield of said product on said substrate, selectivity of the oxidation reaction for said N-(phosphonomethyl)glycine product, quality of product recoverable from said reaction mixture, productivity, emissions in process effluents, stability of catalyst activity, and manufacturing cost.

EXAMPLES

The following examples are simply intended to further illustrate and explain the present invention. This invention, therefore, should not be limited to any of the details in these examples.

The data acquisition parameters for the following examples typically consisted of 8 wave number resolution and 180 spectra (scans) with a data point generated every 145 seconds. For continuous reactions, the number of scans was increased to 360 with a new data point every 5 minutes in an effort to improve the signal to noise ratio. The ultrasonic cleaner was used in an effort to keep the probe clean and was being evaluated at 5 and 15 second pulse durations. The initial work was performed with a mercury cadmium telluride (MCT) detector. Subsequent work was performed using a deuterated triglycine sulfate (DTGS) detector. While not as fast or sensitive as the MCT detector, the DTGS does not require liquid nitrogen cooling. All of the data evaluation was based on partial least squares (PLS) algorithms. The spectral regions chosen for data analysis were based on the known absorbance of each analyte. Example spectra for each analyte in water are found in FIGS. 1–4.

Initial Batch Reaction Monitoring

Figure 5:
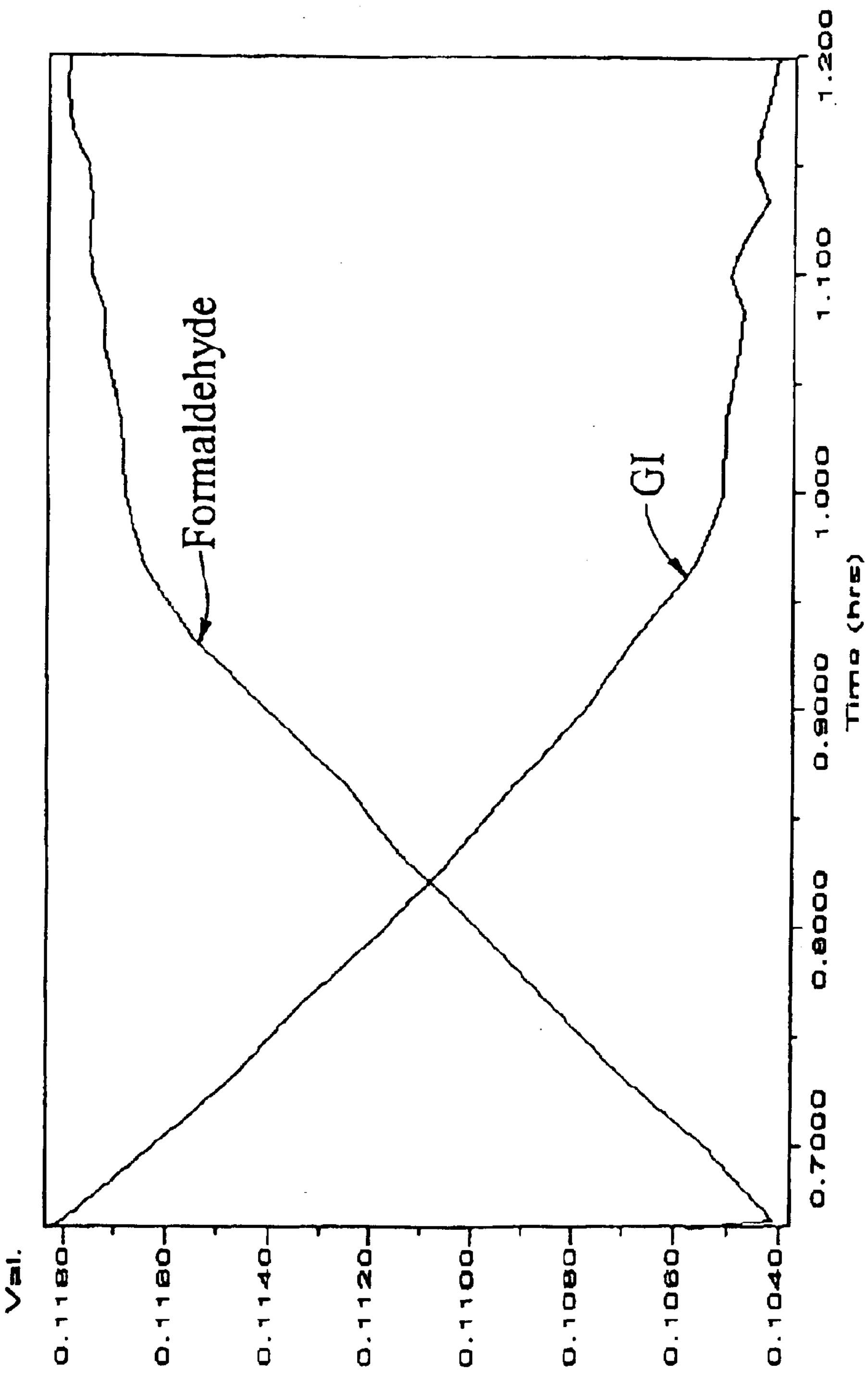
FIG. 5 shows concentration data for formaldehyde and GI determined by FTIR during a batch reaction using a carbon catalyst.
Figure 6:
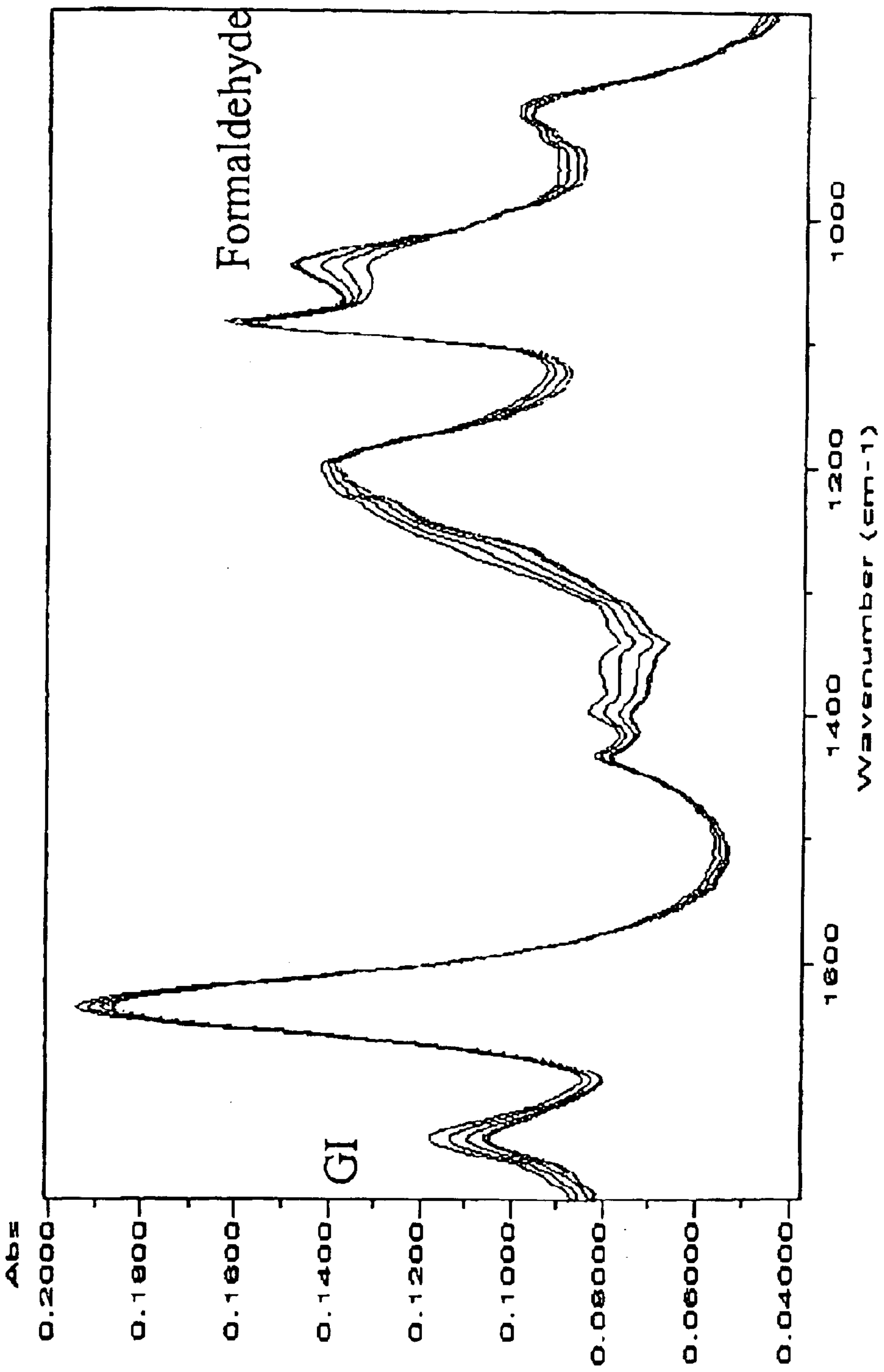
FIG. 6 shows absorbance data collected during a batch reaction using a carbon catalyst.

Reaction monitoring experiments were performed using either a conventional carbon catalyst or a bifunctional catalyst. The FTIR data for the conventional carbon catalyst run indicated that formaldehyde and GI could be tracked in-line for this reaction. As shown in FIG. 5, the growth of formaldehyde with time was tracked until a plateau was reached and the loss of Glyphosate intermediate (GI) was tracked until essentially none remained. The glyphosate and formic acid could not be spectrally distinguished without a set of calibration samples to allow for spectral deconvolution. FIG. 6 shows spectra collected during the run with the spectral regions which were used to track GI and formaldehyde noted. These two analytes demonstrated spectral intensity changes in relatively uncongested regions of the infrared spectrum which allowed for concentration tracking without the use of calibration standard based deconvolution algorithms.

Figure 7:
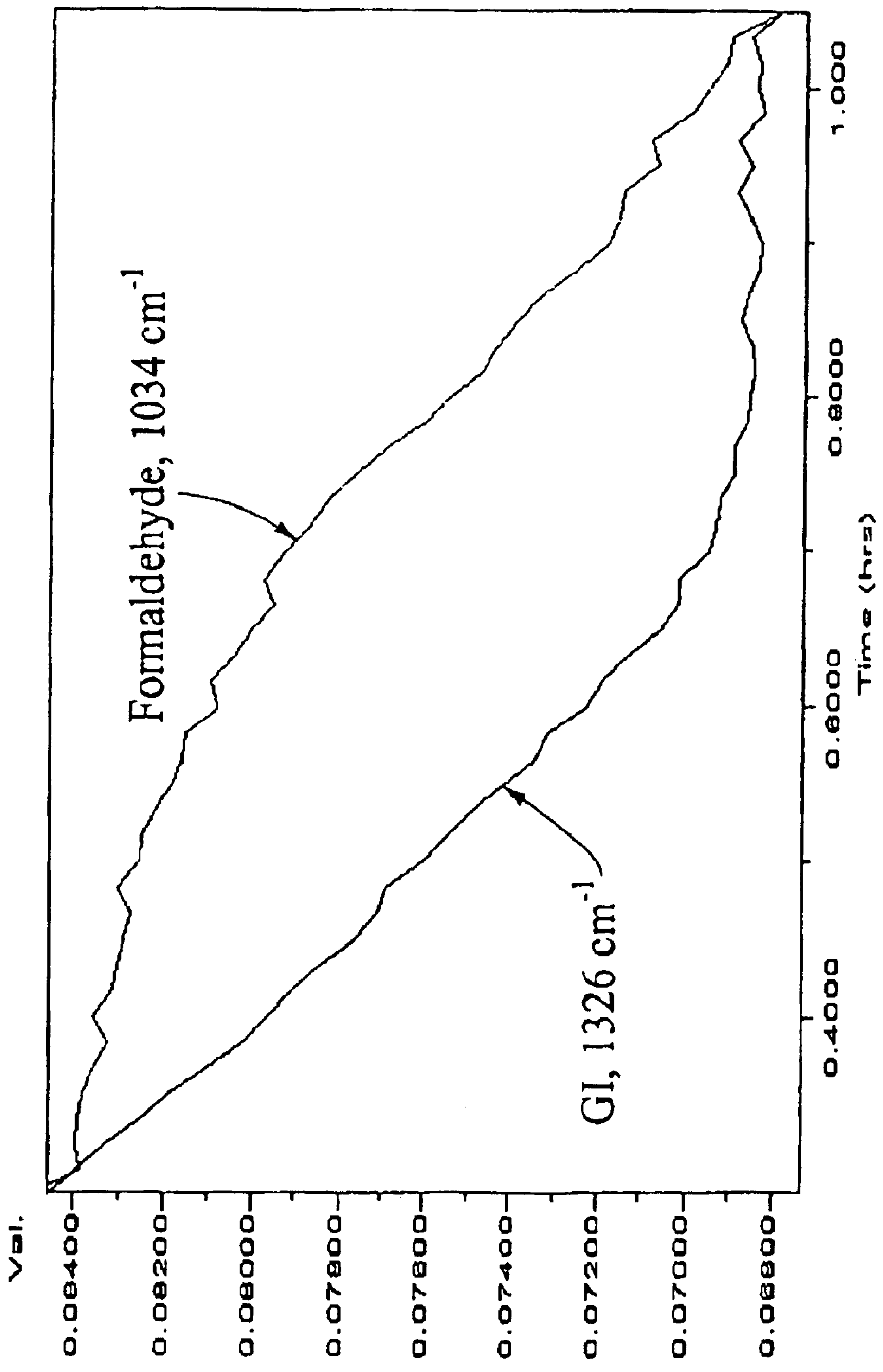
FIG. 7 shows concentration data for formaldehyde and glyphosate intermediate (GI) determined by FTIR during a batch reaction using a bifunctional catalyst.
Figure 8:
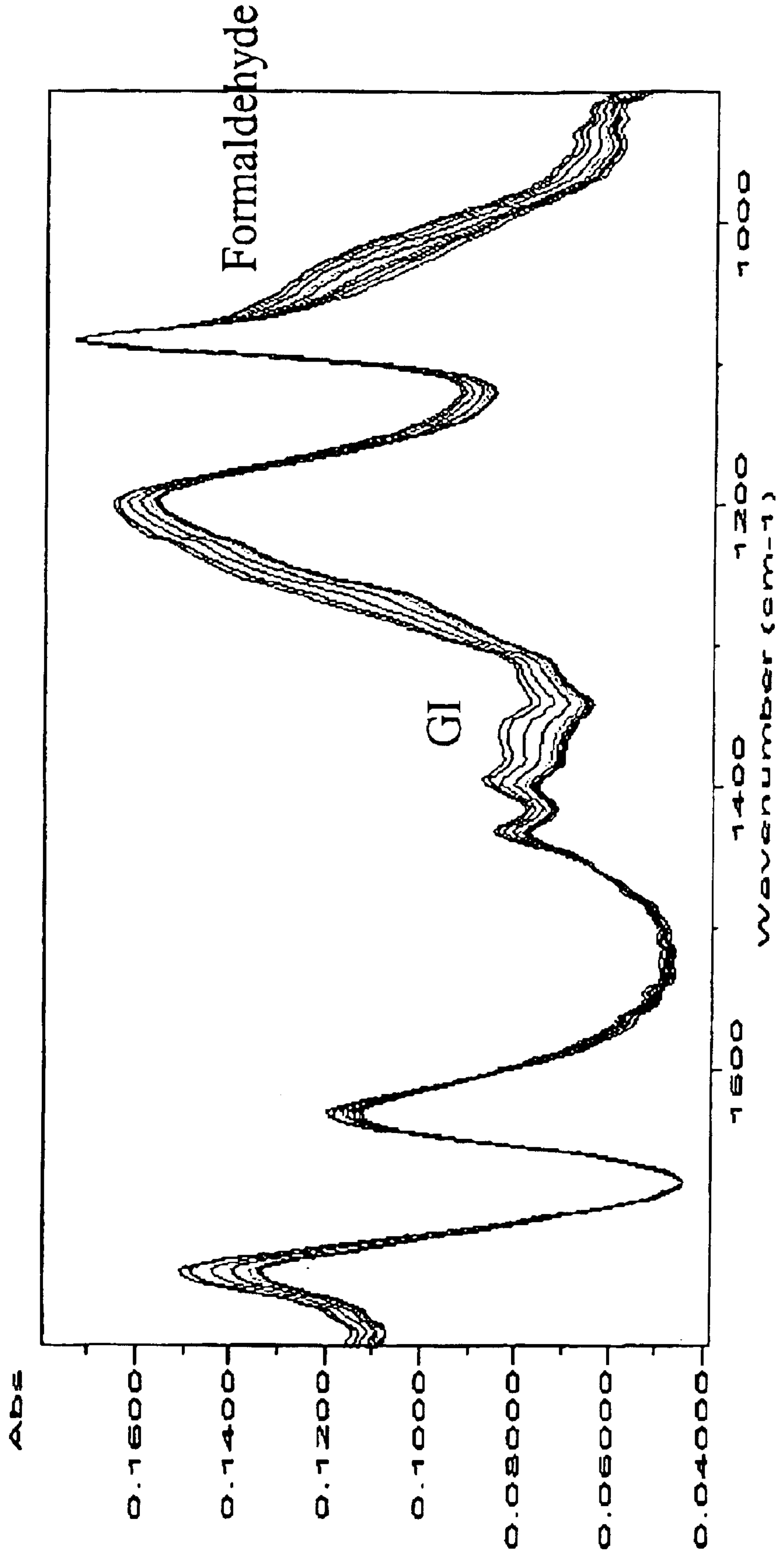
FIG. 8 shows absorbance data collected during a batch reaction using a bifunctional catalyst.
Figure 9:
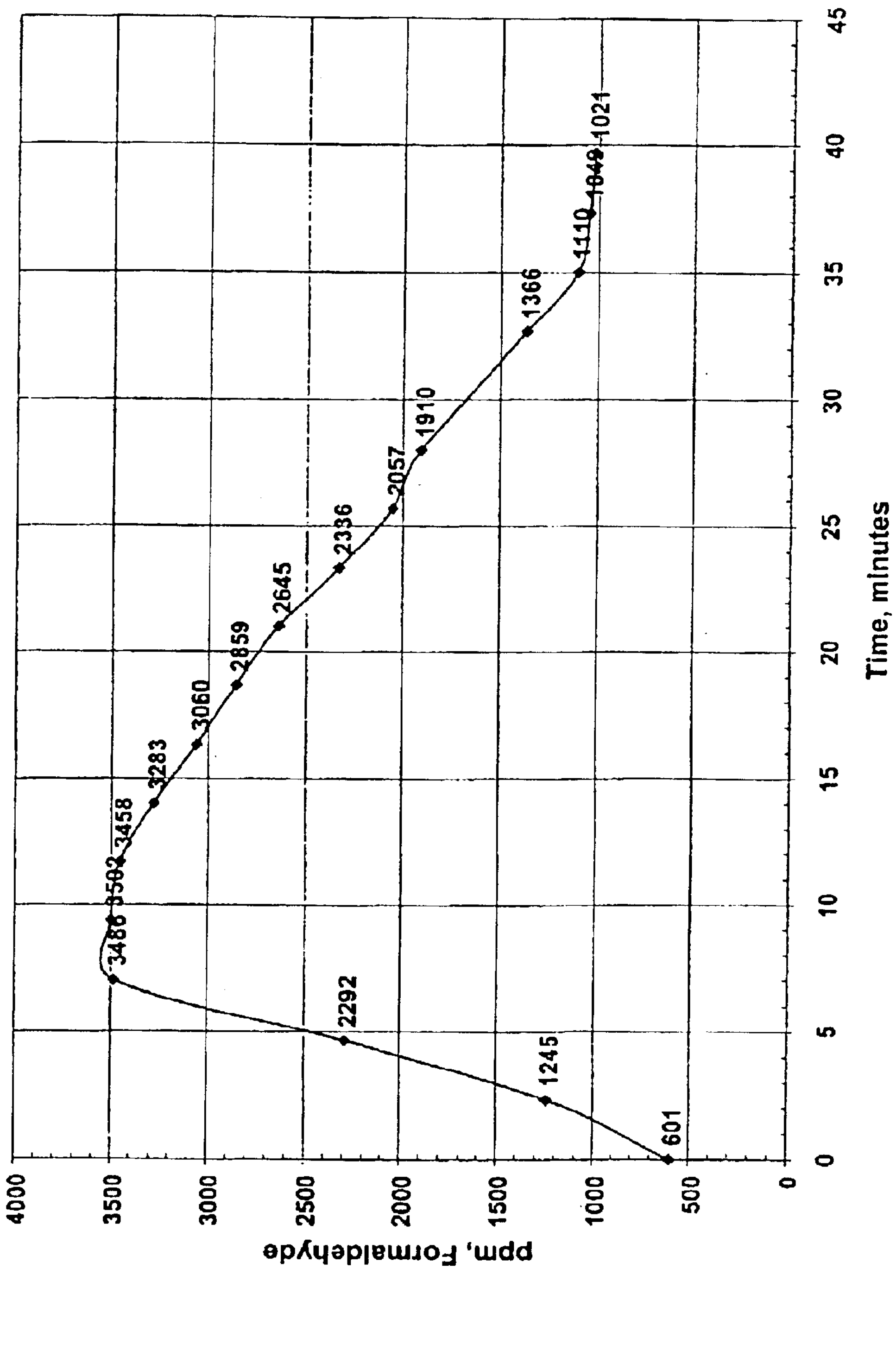
FIG. 9 shows concentration data for formaldehyde determined by FTIR during a batch reaction.
Figure 10:
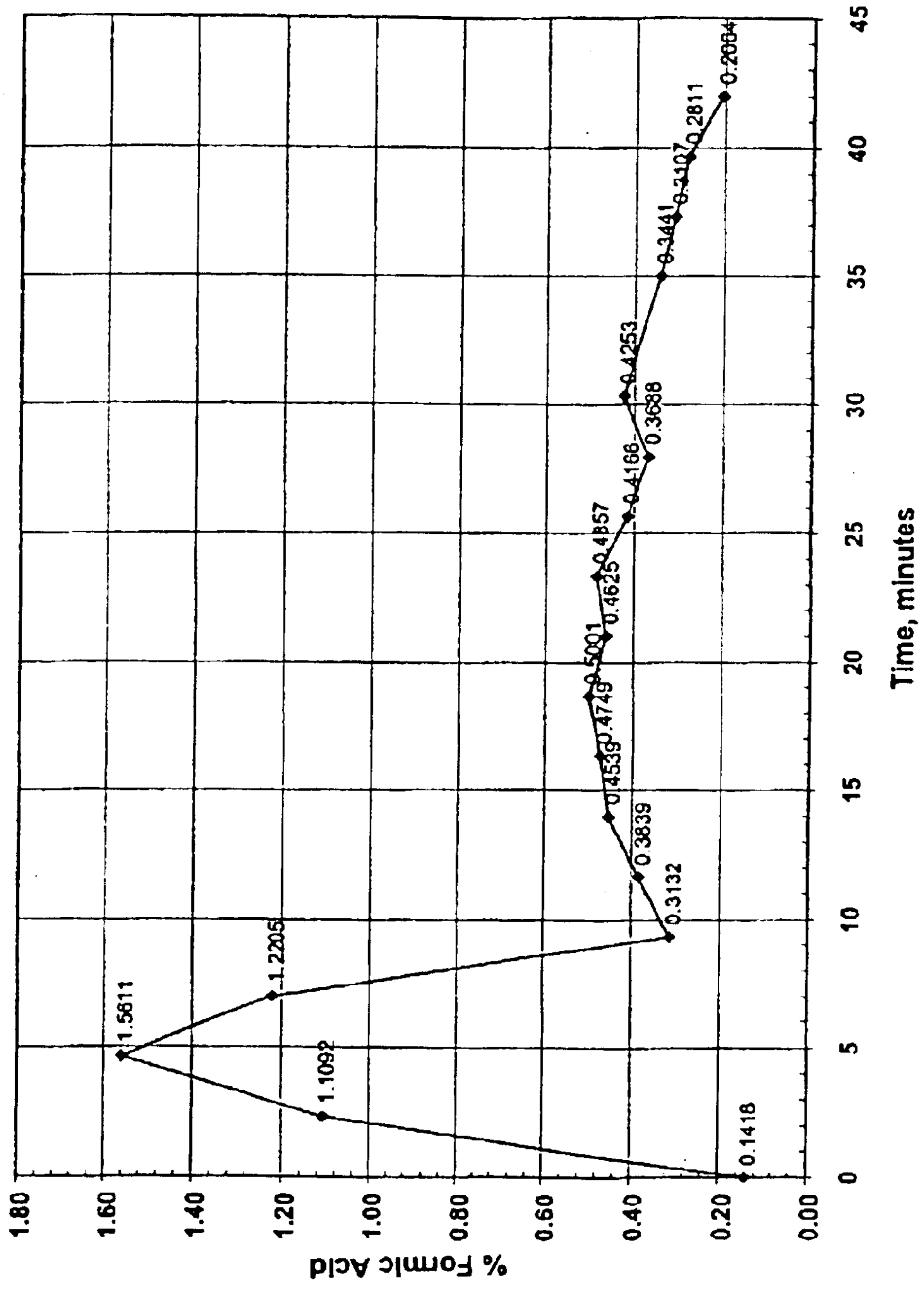
FIG. 10 shows concentration data for formic acid determined by FTIR during a batch reaction.
Figure 11:
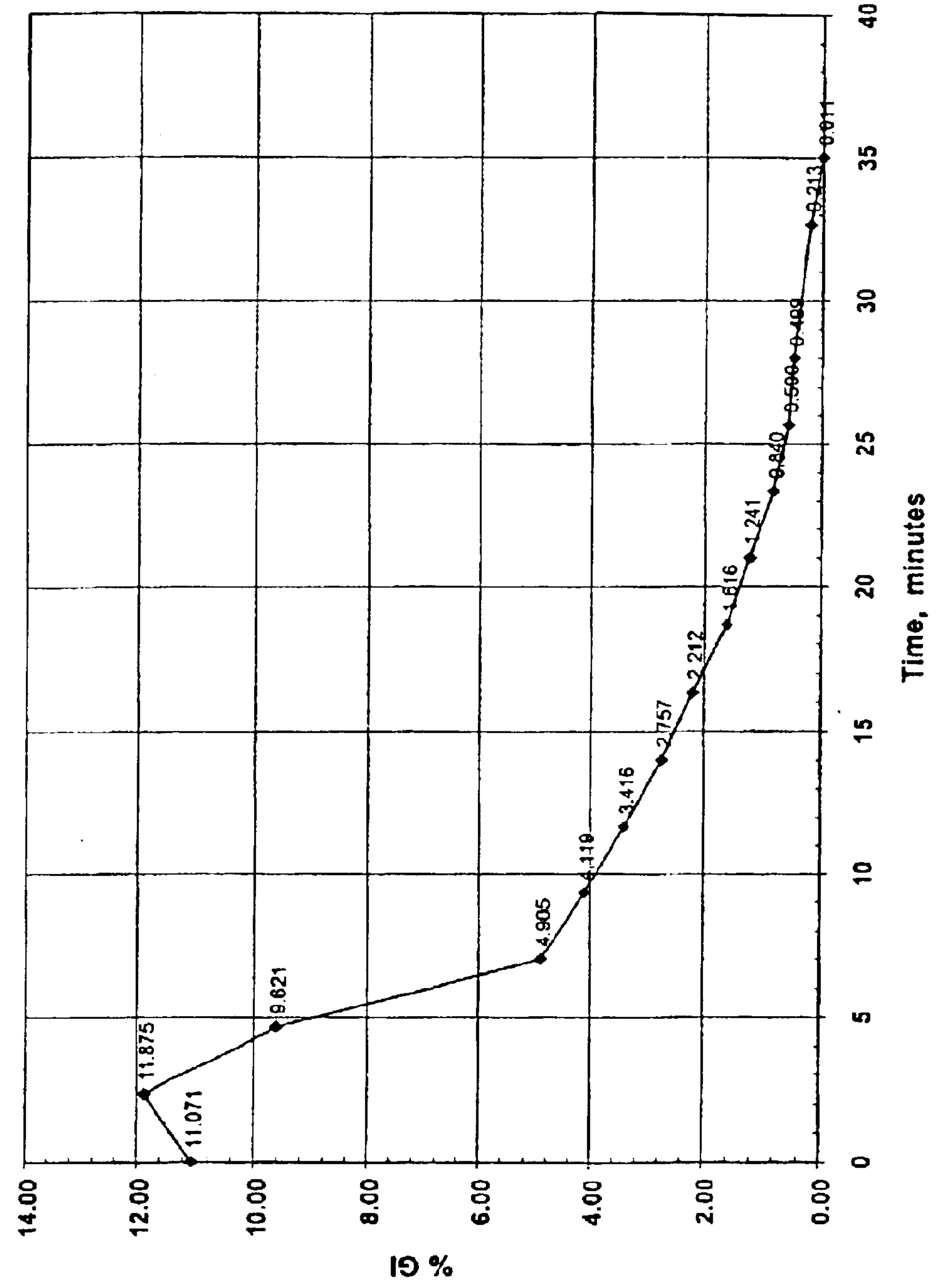
FIG. 11 shows concentration data for glyphosate intermediate (GI) determined by FTIR during a batch reaction.
Figure 12:
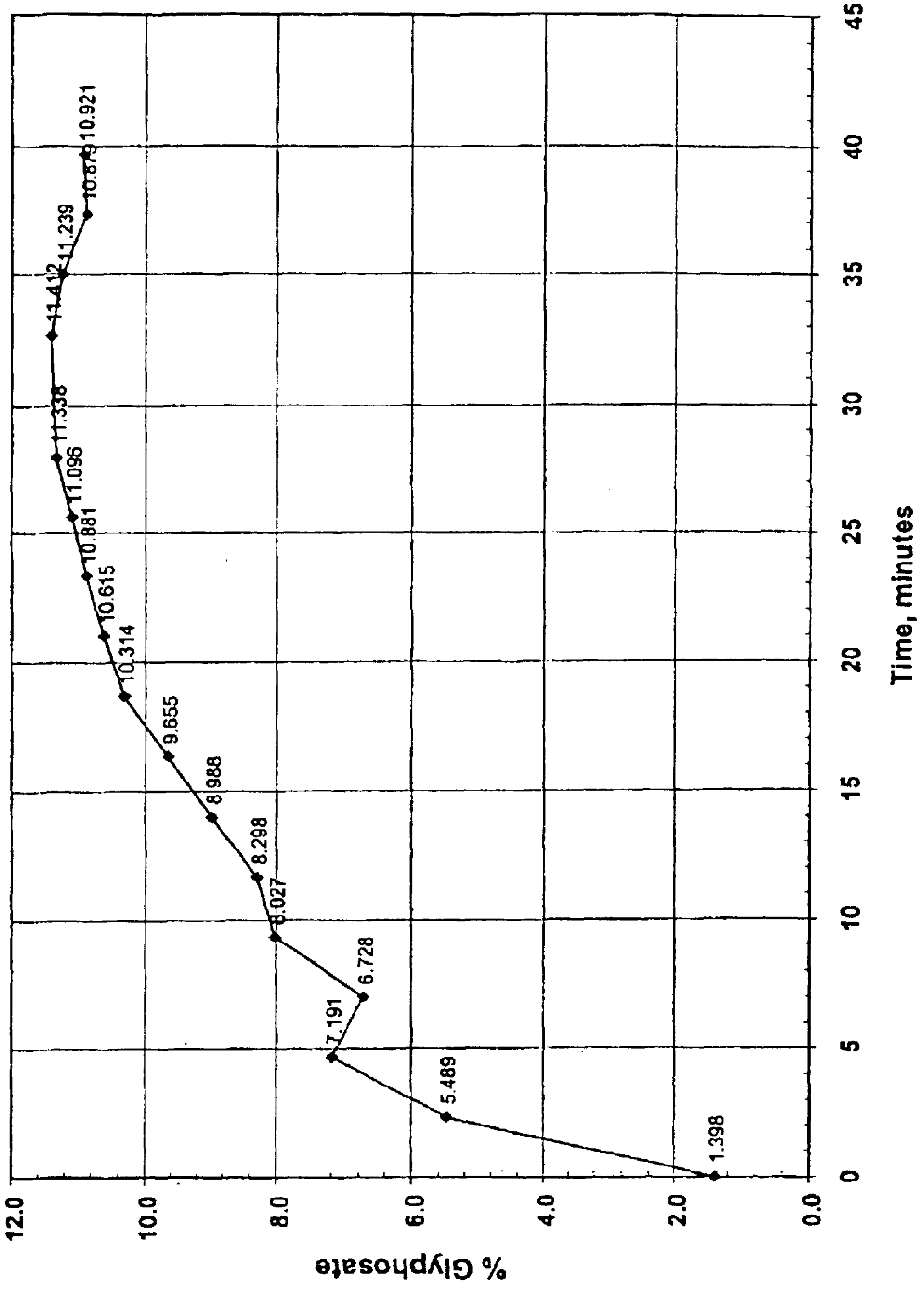
FIG. 12 shows concentration data for glyphosate determined by FTIR during a batch reaction.

The FTIR data for the bifunctional catalyst run also indicated that formaldehyde and GI could be tracked in-line for this reaction, as shown in FIG. 7. Background subtraction issues associated with the bifunctional catalyst run resulted in GI tracking at a lower wave number than for the conventional carbon catalyst run. FIG. 8 contains spectra collected during the run.

Once again, glyphosate and formic acid could not be spectrally distinguished without a set of calibration samples to allow for spectral deconvolution.

The above line FTIR results were promising in terms of tracking relative formaldehyde and GI concentrations during the course of GI to glyphosate reactions. Calibration samples were then generated and calibration models developed in order to quantify formaldehyde and GI and to determine if glyphosate and formic acid could be monitored in-line.

Summary of Lab Scale Reaction In-line FTIR Data

In-line FTIR systems commercially available from ASI Applied Systems (Annapolis, Md.) and Orbital Sciences Corporation (Pomona, Calif.) were used to monitor the GI to glyphosate bifunctional catalyst reaction. Six reactions were run. Reaction 1 used only the ASI system. Reaction 2 used only the Orbital system. Reaction 3 used both systems. Reaction 4 used both systems. Reaction 5 used both systems, but the ASI system was equipped with a DTGS rather than an MCT detector. Reaction 6 used only the ASI system with a new DTGS detector. All of the ASI studies used a nine bounce DiComp ATR probe. All of the Orbital studies used a three bounce DMD-270 ATR probe.

The ASI system exhibited strong absorption bands in the 1600 $cm^{-1}$ and 800 $cm^{-1}$ regions which were not seen with the Orbital system. It was confirmed that these bands are consistent with water absorption and were due to using an air background subtraction with the ASI data and a water background subtraction with the Orbital data.

Samples were taken during each reaction for off-line chromatographic analysis so that FTIR calibration models could be built. Chromatographic data were received for all of the runs, and the following calibration data were generated.

ASI System with MCT Detector 128 scans with 4 $cm^{-1}$ resolution, 1117.30 to 978.30 $cm^{-1}$ spectral region, 4 factors used for prediction, data from Runs 3 & 4, partial least squares (PLS) calibration, 3471 to 912 ppm formaldehyde range, 39 ppm formaldehyde mean error. Leave one out cross validation, 63 ppm formaldehyde mean error.

ASI System with MCT Detector 128 scans with 4 $cm^{-1}$ resolution, 1493.50 to 1117.30 $cm^{-1}$ spectral region, 4 factors used for prediction, data from Runs 3 & 4, PLS calibration, 3.875 to 0% GI range, 0.0469% GI mean error. Leave one out cross validation, 0.0640% GI mean error.

ASI System with MCT Detector 128 scans with 4 $cm^{-1}$ resolution, 976.40 to 1742.50 $cm^{-1}$ spectral region, 6 factors used for prediction, data from Runs 3 & 4, PLS calibration, 1866 ppm to 5058 ppm formic acid range, 62 ppm formic acid mean error. Leave one out cross validation, 100 ppm formic acid mean error.

ASI System with MCT Detector 128 scans with 4 $cm^{-1}$ resolution, 1463 to 976 $cm^{-1}$ spectral region, 4 factors used for prediction, data from Runs 3 & 4, PLS calibration, 2.245 to 5.584% glyphosate range, 0.0457% glyphosate mean error. Leave one out cross validation, 0.0600% glyphosate mean error.

ASI System with DTGS Detector 128 scans with 4 $cm^{-1}$ resolution, 1117.30 to 978.30 $cm^{-1}$ spectral region, 4 factors used for prediction, data from Run 5, PLS calibration, 2357 to 731 ppm formaldehyde range, 7 ppm formaldehyde mean error. Leave one out cross validation, 36 ppm formaldehyde mean error.

ASI System with DTGS Detector 128 scans with 4 $cm^{-1}$ resolution, 1501.30 to 928.20 $cm^{-1}$ spectral region, 4 factors used for prediction, data from Run 5, PLS calibration, 3.151 to 0% GI range, 0.0217% GI mean error. Leave one out cross validation, 0.0604% GI mean error.

ASI System with DTGS Detector 128 scans with 4 $cm^{-1}$ resolution, 1742.50 to 976.40 $cm^{-1}$ spectral region, 4 factors used for prediction, data from Run 5, PLS calibration, 4755 to 2980 ppm formic acid range, 38 ppm formic acid mean error. Leave one out cross validation, 174 ppm formic acid mean error.

ASI System with DTGS Detector 128 scans with 4 $cm^{-1}$ resolution, 1463 to 976 $cm^{-1}$ spectral region, 3 factors used for prediction, data from Run 5, PLS calibration, 3.217 to 5.712% glyphosate range, 0.0477% glyphosate mean error. Leave one out cross validation, 0.0839% glyphosate mean error.

ASI System with New DTGS Detector 80 scans with 8 $cm^{-1}$ resolution, 1115 to 945 $cm^{-1}$ spectral region, 4 factors used for prediction, data from Run 6, PLS calibration, 3761 to 420 ppm formaldehyde range, 38 ppm formaldehyde mean error. Leave one out cross validation, 62 ppm formaldehyde mean error.

ASI System with New DTGS Detector 80 scans with 8 $cm^{-1}$ resolution, 1779 to 918 $cm^{-1}$ spectral region, 4 factors used for prediction, data from Run 6, PLS calibration, 1.711 to 0% GI range, 0.121% GI mean error. Leave one out cross validation, 0.224% GI mean error.

ASI System with New DTGS Detector 80 scans with 8 $cm^{-1}$ resolution, 1742 to 976 $cm^{-1}$ spectral region, 5 factors used for prediction, data from Run 6, PLS calibration, 5142 to 1167 ppm formic acid range, 70 ppm formic acid mean error. Leave one out cross validation, 184 ppm formic acid mean error.

Orbital System with MCT Detector 100 scans with 4 $cm^{-1}$ resolution, 1139 to 900 $cm^{-1}$ spectral region, 4 factors used for prediction, data from Run 4, PLS calibration, 3241 to 502 ppm formaldehyde range, 36 ppm formaldehyde mean error.

Orbital System with MCT Detector 100 scans with 4 $cm^{-1}$ resolution, 1300 to 900 $cm^{-1}$ spectral region, 4 factors used for prediction, data from Run 2, PCR calibration, 4310 to 1571 ppm formaldehyde range, 190 ppm formaldehyde standard error of calibration.

Orbital System with MCT Detector 100 scans with 4 $cm^{-1}$ resolution, 1300 to 900 $cm^{-1}$ spectral region, 5 factors used for prediction, data from Run 2, PCR calibration, 6265 to 1093 ppm formic acid range, 230 ppm formic acid standard error of calibration.

The instrumentation for the following experiments consists of a nine bounce DiComp probe, a ReactIR MP spectrometer, and the appropriate ASI software for instrument control, data collection, and data manipulation.

Batch Reaction Analyses

An instrument was located in a batch reactor. Calibration models were generated during that time and are summarized in Table 1.

TABLE 1

| | Formaldehyde | Formic Acid | Glyphosate | GI |
|---|---|---|---|---|
| Concentration Range | 134 to 5628 ppm | 0.26 to 0.87% | 6.679 to 10.555% | ND to 3.838% |
| Spectral Range, $cm^{-1}$ | 1115 to 945 | 1459 to 1177.2 | 1459 to 1281.5 945.7 to 864.6 | 1459 to 1065.3 |
| Number of Factors | 5 | 5 | 5 | 5 |
| Number of Standards | 54 | 45 | 50 | 48 |
| PLS Mean Error | 148 ppm | 0.039% | 0.205% | 0.152% |

FIGS. 9–12 show plots of analyte tracking during a batch reaction. In earlier batch work, it was noted that usable spectra were not available until the GI was completely dissolved. The spectral differences indicated that solid GI was perhaps being trapped in the concave probe. This observation led to the use of probe which had a flat rather than concave surface. When the flat probe was used, no difference in spectra was observed whether or not all of the GI was soluble.

Figure 13:
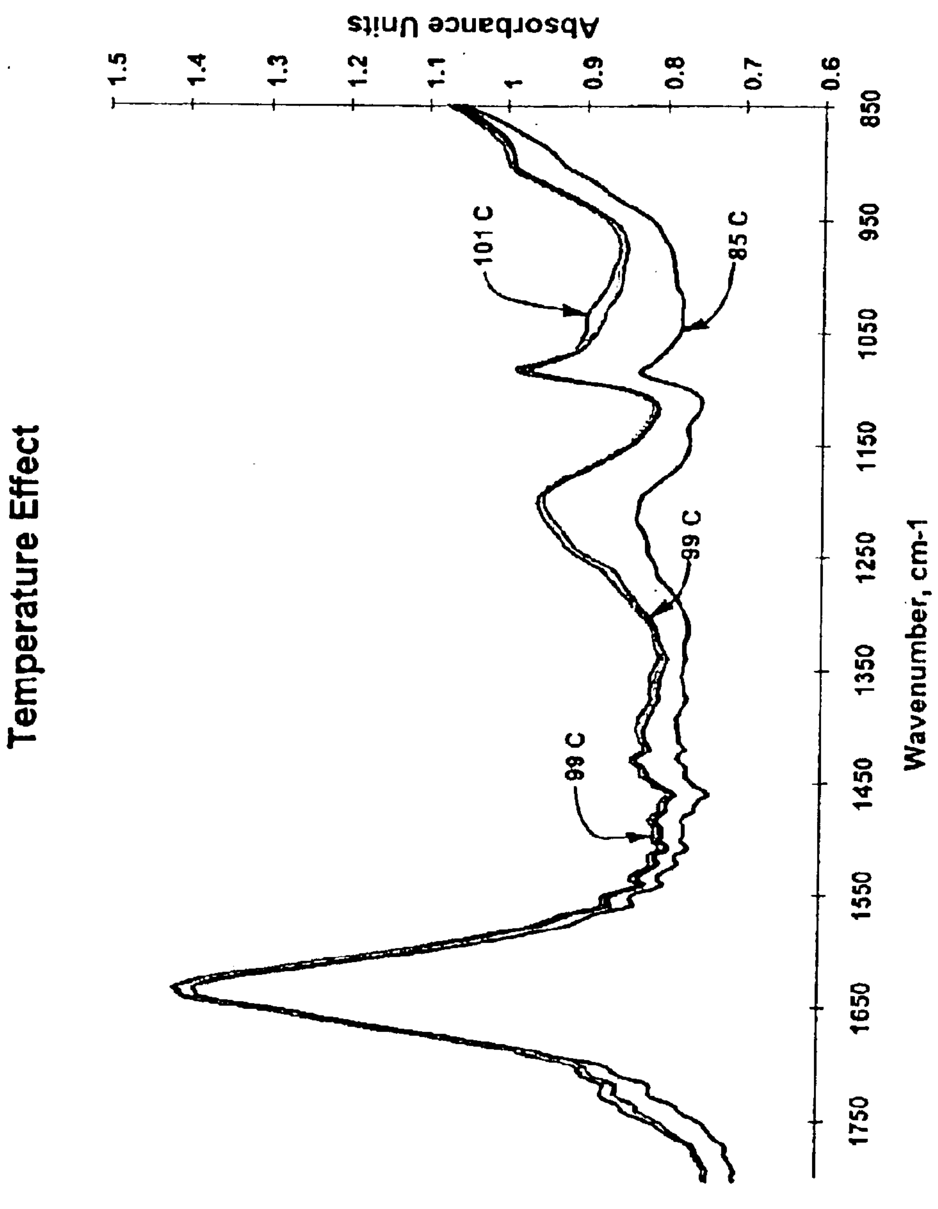
FIG. 13 shows the effect temperature has on absorbance spectra.

Temperature was also identified as an important variable during the batch experiment. FIG. 13 shows the effect of reaction temperature on spectral intensity.

Continuous Reaction Monitoring

An FTIR was installed in the final reaction effluent stream of a pilot scale continuous process using two continuous reactors in series to monitor the continuous GI to glyphosate reaction. In-line FTIR was used to monitor the process. The batch models developed for the batch process were not applicable for use with the continuous process. Initial model conditions for monitoring the continuous reactor are found in Table 2.

TABLE 2

| | GI | Glyphosate | Formic Acid | Formaldehyde |
|---|---|---|---|---|
| # of Standards | 17 | 25 | 28 | 28 |
| Concentration Range | 0.0417 to 0.7968% | 4.299 to 6.152% | 0.2965 to 1.277% | 292 to 3176 ppm |
| Spectral Range | 1065.30 to 1397.30 $cm^{-1}$ | 1281.50 to 1405.00 $cm^{-1}$ & 864.00 to 945.70 $cm^{-1}$ | 1177.20 to 1393.40 $cm^{-1}$ | 945.00 to 1115.00 $cm^{-1}$ |
| # of Factors | 5 | 5 | 4 | 5 |
| Mean Error in Std Curve | 0.0224% | 0.0721% | 0.0219% | 53 ppm |

Figure 14:
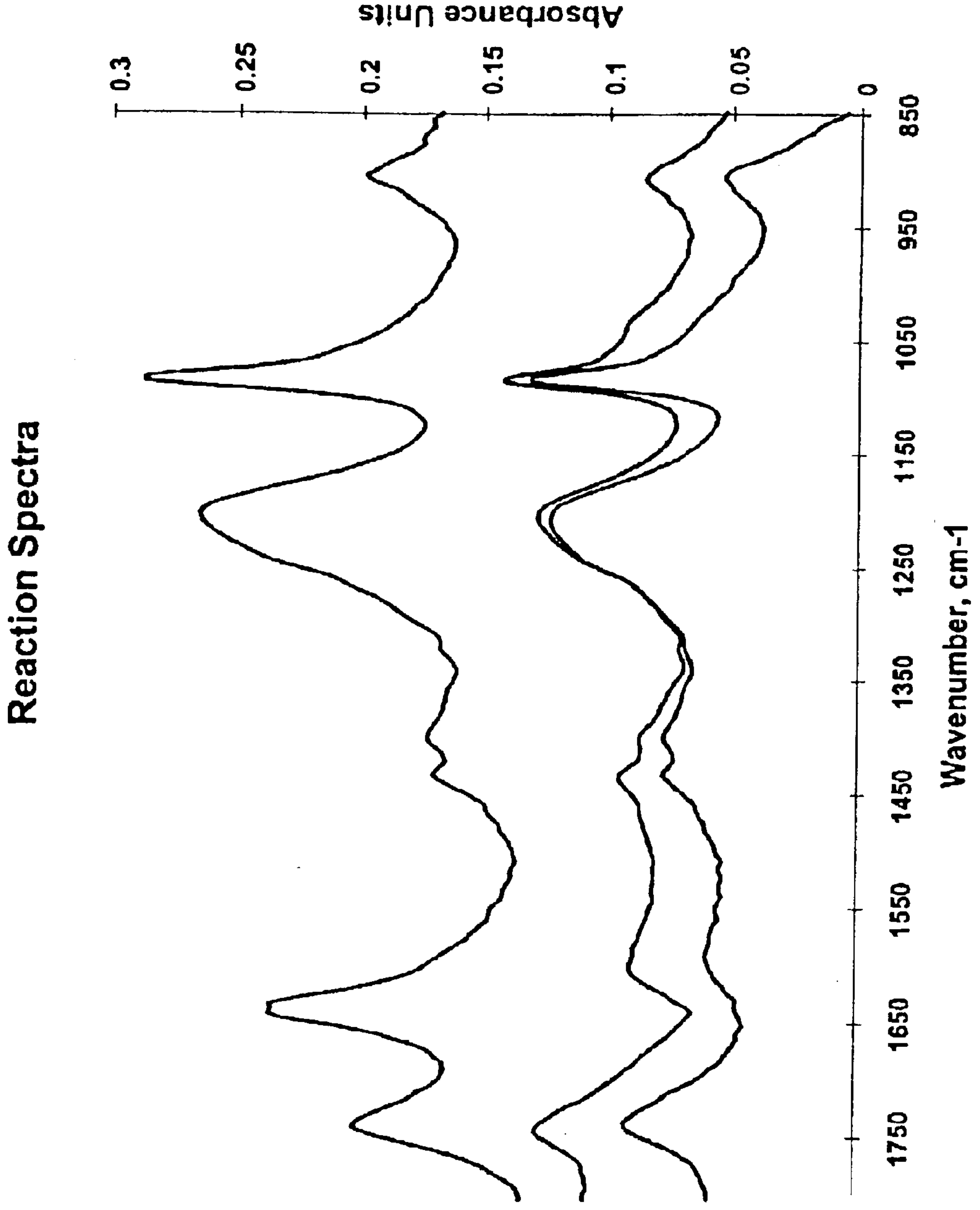
FIG. 14 shows absorbance spectra from a continuous reaction process.
Figure 15:
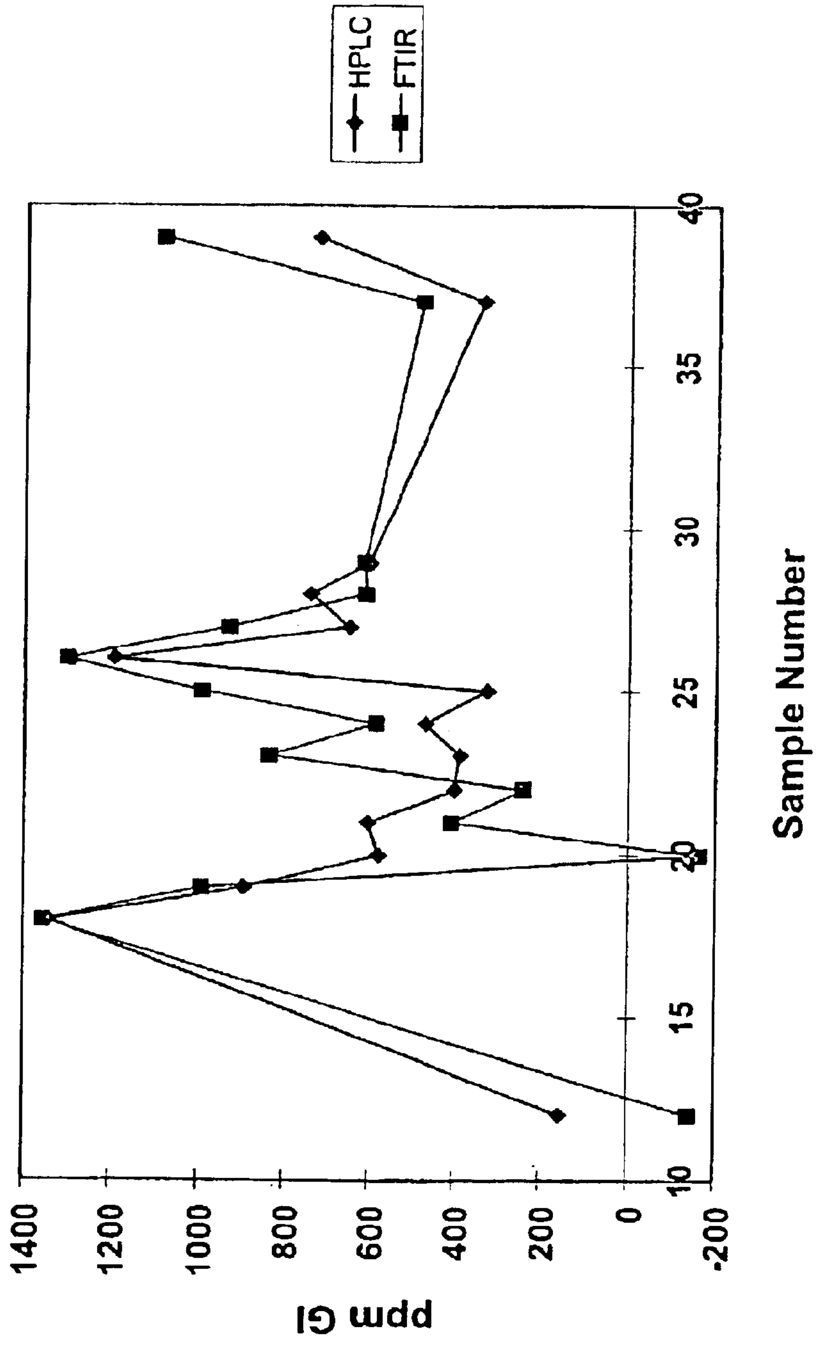
FIG. 15 shows a comparison of the concentration of glyphosate intermediate (GI) measured by in-line FTIR verses High pressure liquid chromatography (HPLC).
Figure 16:
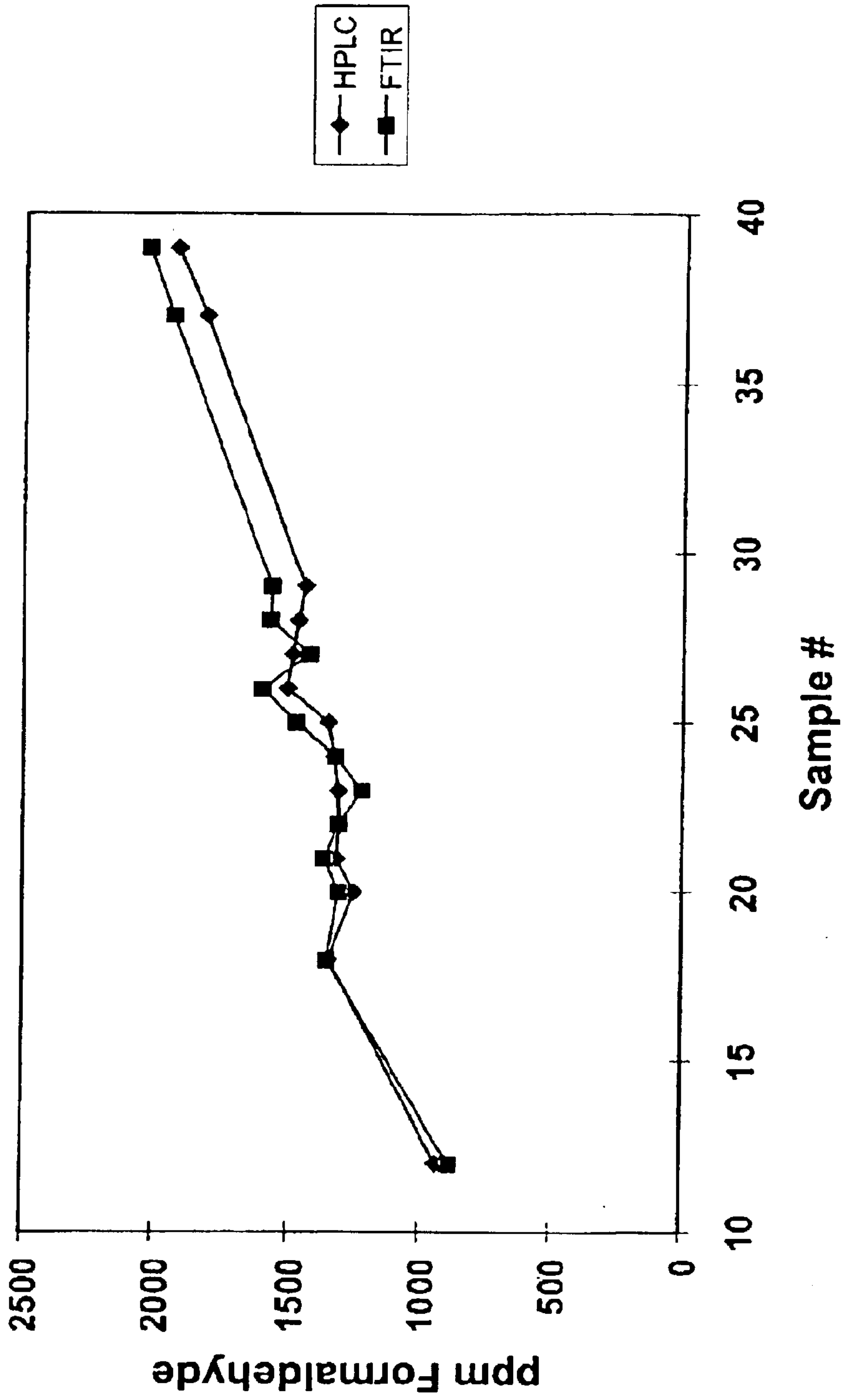
FIG. 16 shows a comparison of the concentration of formaldehyde measured by in-line FTIR verses High pressure liquid chromatography (HPLC).
Figure 17:
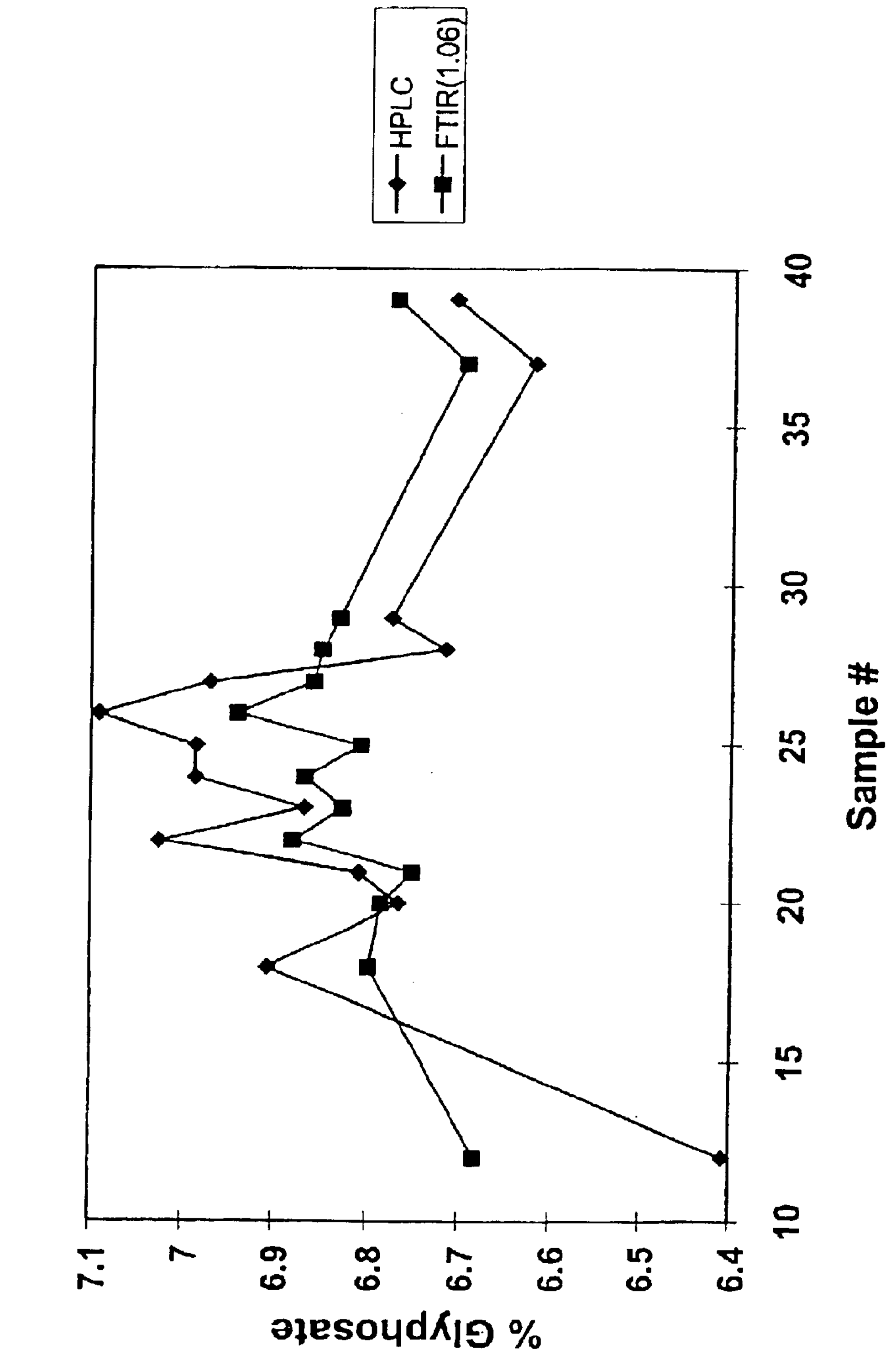
FIG. 17 shows a comparison of the concentration of glyphosate measured by in-line FTIR verses High pressure liquid chromatography (HPLC).
Figure 18:
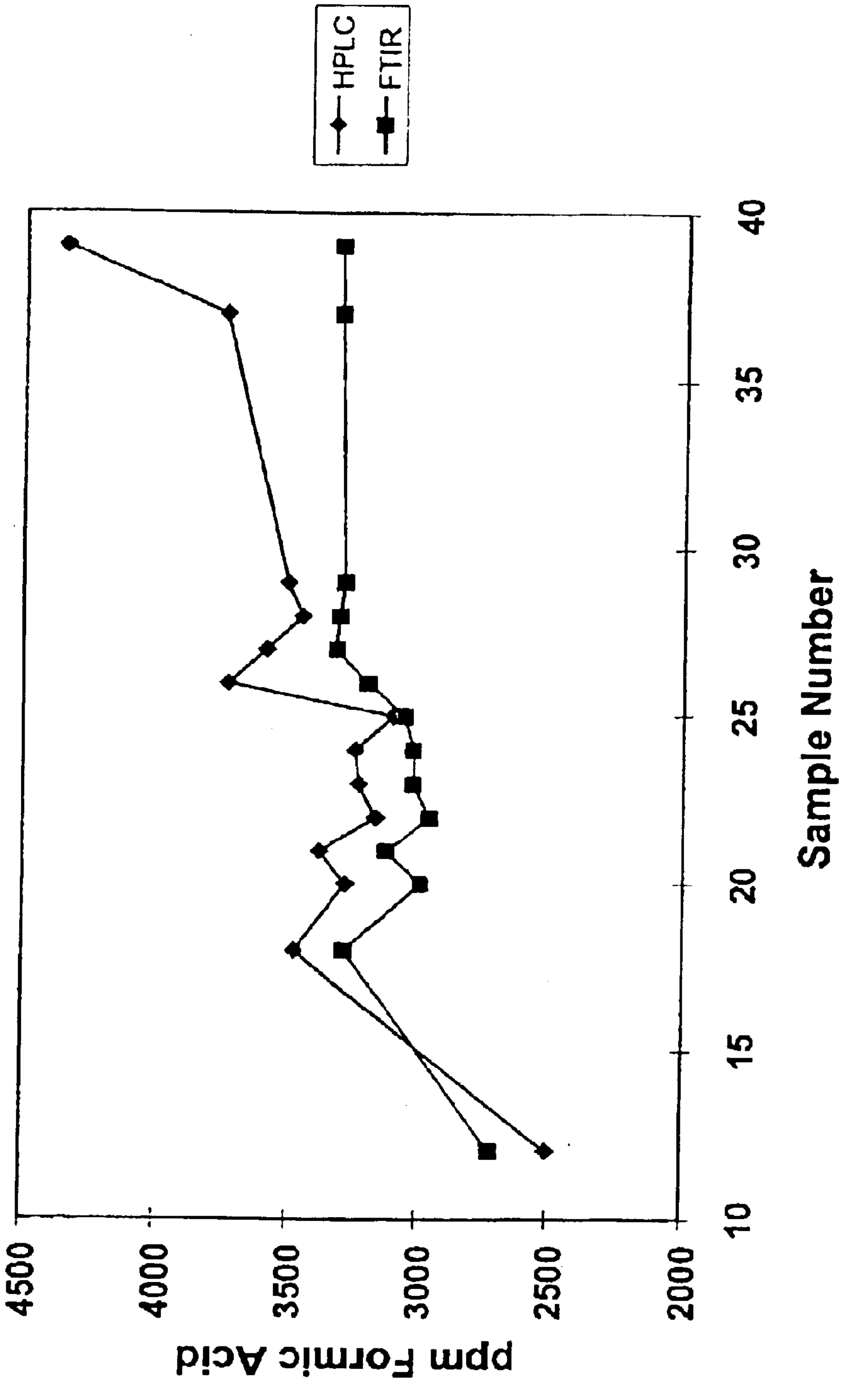
FIG. 18 shows a comparison of the concentration of formic acid measured by in-line FTIR verses High pressure liquid chromatography (HPLC).

Typical reaction spectra are found in FIG. 14. Comparisons of in-line FTIR and HPLC data are found in the FIGS. 15 through 18.

Changes in the process resulted in a decrease in formic acid concentration from the 2000 to 5000 ppm range to the 300 to 600 ppm range. This order of magnitude reduction in formic acid concentration resulted in a matrix that had not been modeled and thus greatly impacted the various models' prediction capabilities. With some model modification, the GI, glyphosate, and formaldehyde models were improved but the formic acid model remained off by a factor of about 10 in its prediction (i.e. model predicted 4000 ppm while HPLC assay was 400 ppm). Upon reexamination of the complete formic acid IR spectrum, it was noted that a strong absorption band exists around 1721 $cm^{-1}$. This band is close to the 1600 $cm^{-1}$ water region which is subtracted out as a background and thus can be inconsistent and difficult to quantify. In an effort to minimize the effects of the water subtraction, the region away from the water subtraction, 1787 $cm^{-1}$ to 1710 $cm^{-1}$, was used in the revised formic acid model. This resulted in reasonable formic acid prediction values for the low formic acid spectra. This revised formic acid model represented an improvement in formic acid prediction capability.

In another example, two in-line FTIR instruments were installed in a commercial scale continuous reaction system, one in the intermediate reaction effluent from the first reactor, and one in the reaction effluent from the second reactor. Chemometric models for GI, glyphosate, formic acid, and formaldehyde developed for the pilot scale reaction effluent were initially used for both the intermediate reaction mixture and the final reaction mixture of the commercial scale process. The chemometric models, provided reasonable trending information for the final reaction mixture, but provided limited information for the intermediate reaction mixture. New chemometric models were developed for the commercial scale continuous process. Example model data are found in Tables 3 and 4.

TABLE 3

| | Intermediate reaction mixture models | | | |
|---|---|---|---|---|
| | GI | Glyphosate | Formic Acid | Formaldehyde |
| # of Standards | 30 | 30 | 19 | 36 |
| Concentration Range | 684 to 4601 ppm | 5.539 to 7.467% | 0.199 to 0.370% | 509 to 1356 ppm |
| Spectral Range | 1397.20 to 1065.30 $cm^{-1}$ | 1405.00 to 1281.50 $cm^{-1}$ & 945.70 to 883.90 $cm^{-1}$ | 1787.10 to 1790 $cm^{-1}$ | 1073.00 to 1000.00 $cm^{-1}$ |
| # of Factors | 6 | 4 | 6 | 4 |
| Mean Error in Std. Curve | 167 ppm | 0.164% | 0.012% | 71 ppm |

TABLE 4

| Final reaction mixture models | | | | |
|---|---|---|---|---|
| | GI | Glyphosate | Formic Acid | Formaldehyde |
| # of Standards | 49 | 44 | 45 | 47 |
| Concentration Range | 278 to 1756 ppm | 4.511 to 8.250% | 0.110 to 0.341% | 108 to 392 ppm |
| Spectral Range | 1397.20 to 1065.30 $cm^{-1}$ | 1405.00 to 1281.50 $cm^{-1}$ & 945.70 to 883.90 $cm^{-1}$ | 1787.10 to 1790 $cm^{-1}$ & 1393.40 to 1177.20 $cm^{-1}$ | 1073.00 to 1000.00 $cm^{-1}$ |
| # of Factors | 6 | 5 | 4 | 5 |
| Mean Error in Std. Curve | 100 ppm | 0.200% | 0.026% | 30 ppm |

The GI monitoring goals with regard to the final reaction mixture were developed for particularly low concentrations. The final reaction mixture GI concentration target was 1000 ppm for the pilot scale process. The commercial scale final reaction mixture GI concentration target was changed first to 800 ppm and then to 500 ppm. In an effort to improve the signal to noise ratio (S/N), the number of scans was increased from 180 to 360. This results in S/N increase of approximately 30%.

In view of the above, it will be seen that the several objects of the invention are achieved. As various changes could be made in the above-described process without departing from the scope of the invention, it is intended that all matters contained in the above description be interpreted as illustrative and not in a limiting sense. In addition, when introducing elements of the present invention or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

We claim:

1. A method for determining the concentration of an analyte of an aqueous mixture comprising N-(phosphonomethyl)iminodiacetic acid, a salt of N-(phosphonomethyl)iminodiacetic acid, an ester of N-(phosphonomethyl)iminodiacetic acid), N-(phosphonomethyl)glycine, a salt of N-(phosphonomethyl)glycine, an ester of N-(phosphonomethyl)glycine), formaldehyde, formic acid, N-methyl-N-(phosphonomethyl)glycine, N-methyl-aminomethylphosphonic acid, aminomethylphosphonic acid, or mixtures thereof, the method comprising:

measuring an electromagnetic absorbance spectrum for the aqueous mixture over an infrared wavenumber range of from about 200 $cm^{-1}$ to about 5000 $cm^{-1}$ using a Fourier transform infrared spectrometer which uses an internal reflectance sensor to sample the electromagnetic absorbance of the mixture, the internal reflectance sensor being an attenuated total reflectance probe having a sampling surface comprising diamond; and using data from the electromagnetic absorbance spectrum in a chemometric model to determine the concentration of the analyte in the aqueous mixture, the chemometric model being a mathematical relationship between the concentration of the analyte in the aqueous mixture as a function of the electromagnetic absorbance spectrum of the mixture.

2. A method for determining the concentration of an analyte of an aqueous mixture comprising N-(phosphonomethyl)iminodiacetic acid, a salt of N-(phosphonomethyl)iminodiacetic acid, an ester of N-(phosphonomethyl)iminodiacetic acid), N-(phosphonomethyl)glycine, a salt of N-(phosphonomethyl)glycine, an ester of N-(phosphonomethyl)glycine), formaldehyde, formic acid, N-methyl-N-(phosphonomethyl)glycine. N-methyl-aminomethylphosphonic acid, aminomethylphosphonic acid, or mixtures thereof, the method comprising:

measuring an electromagnetic absorbance spectrum for the aqueous mixture over an infrared wavenumber range of from about 200 $cm^{-1}$ to about 5000 $cm^{-1}$ using a Fourier transform infrared spectrometer which uses a mercury cadmium telluride detector; and using data from the electromagnetic absorbance spectrum in a chemometric model to determine the concentration of the analyte in the aqueous mixture, the chemometric model being a mathematical relationship between the concentration of the analyte in the aqueous mixture as a function of the electromagnetic absorbance spectrum of the mixture.

3. A method for determining the concentration of an analyte of a reaction mixture produced in a process for preparing a N(phosphonomethyl)glycine product by oxidizing a N-(phosphonomethyl)iminodiacetic acid substrate, the reaction mixture comprising N-(phosphonomethyl) iminodiacetic acid, a salt of N-(phosphonomethyl) iminodiacetic acid, an ester of N-(phosphonomethyl) iminodiacetic acid), N-(phosphonomethyl)glycine, a salt of N-(phosphonomethyl)glycine, an ester of N-(phosphonomethyl)glycine), formaldehyde, formic acid, N-methyl-N-(phosphonomethyl)glycine, N-methyl-aminomethylphosphonic acid, aminomethylphosphonic acid, or mixtures thereof, the method comprising:

measuring an electromagnetic absorbance spectrum for the reaction mixture over an infrared wavenumber range of from about 200 $cm^{-1}$ to about 5000 $cm^{-1}$; and using data from the electromagnetic absorbance spectrum in a chemometric model to determine the concentration of the analyte in the reaction mixture, the chemometric model being a mathematical relationship between the concentration of the analyte in the aqueous reaction mixture as a function of the electromagnetic absorbance spectrum of the mixture.

4. The method of claim 3 wherein the reaction mixture in the process for preparing a N-(phosphonomethyl)glycine product by oxidizing a N-(phosphonomethyl)iminodiacetic acid substrate is measured in-situ.

5. The method of claim 3 wherein the analyte is N-(phosphonomethyl)iminodiacetic acid and the concentration of N-(phosphonomethyl)iminodiacetic acid in the reaction mixture is within a range of from about 50 ppm to about 4% by weight.

6. The method of claim 3 wherein the analyte is N-(phosphonomethyl)iminodiacetic acid and the concentration of N-(phosphonomethyl)iminodiacetic acid in the reaction mixture is within a range of from 200 ppm to about 4,500 ppm.

7. The method of claim 3 wherein the analyte is N-(phosphonomethyl)glycine and the concentration of N-(phosphonomethyl)glycine in the reaction mixture is within a range of from about 5% to about 10% by weight.

8. The method of claim 3 wherein the analyte is N-(phosphonomethyl)glycine and the concentration of N-(phosphonomethyl)glycine in the reaction mixture is within a range of from about 4% to about 8% by weight.

9. The method of claim 3 wherein the analyte is formaldehyde and the concentration of formaldehyde in the reaction mixture is within a range of from about 130 ppm to about 6,000 ppm.

10. The method of claim 3 wherein the analyte is formaldehyde and the concentration of formaldehyde in the reaction mixture is within a range of from about 250 ppm to about 4,500 ppm.

11. The method of claim 3 wherein the analyte is formaldehyde and the concentration of formaldehyde in the reaction mixture is within a range of from about 100 ppm to about 400 ppm.

12. The method of claim 3 wherein the analyte is formic acid and the concentration of formic acid in the reaction mixture is within a range of from about 0.3% to about 1.3% by weight.

13. The method of claim 3 wherein the analyte is formic acid and the concentration of formic acid in the reaction mixture is within a range of from about 0.1% to about 0.4% by weight.

14. A method for determining the concentration of an analyte of an aqueous mixture comprising N-(phosphonomethyl)iminodiacetic acid, a salt of N-(phosphonomethyl)iminodiacetic acid, an ester of N-(phosphonomethyl)iminodiacetic acid), N-(phosphonomethyl)glycine, a salt of N-(phosphonomethyl)glycine, an ester of N-(phosphonomethyl)glycine), formaldehyde, formic acid, N-methyl-N-(phosphonomethyl)glycine, N-methyl-aminomethylphosphonic acid, aminomethylphosphonic acid, or mixtures thereof, the method comprising:

measuring an electromagnetic absorbance spectrum for the aqueous mixture over an infrared wavenumber range of from about 200 $cm^{-1}$ to about 5000 $cm^{31\ 1}$; and using data from the electromagnetic absorbance spectrum in a chemometric model to determine the concentration of the analyte in the aqueous mixture, the chemometric model being a mathematical relationship between the concentration of the analyte in the aqueous mixture as a function of the electromagnetic absorbance spectrum of the mixture, the chemometric model for an analyte is being determined by measuring the electromagnetic absorbance spectrum for at least 10 aqueous mixture standards having a known concentration of the analyte to be modeled and performing a multivariate mathematical regression analysis using the analyte concentration and electromagnetic absorbance spectra to determine a chemometric model representing the analyte concentration as a function of the electromagnetic absorbance spectrum.

15. The method of claim 14 wherein the multivariate mathematical regression analysis is a partial least squares analysis.

16. The method of claim 14 wherein at least 20 aqueous mixture standards are used.

17. The method of claim 14 wherein at least 50 aqueous mixture standards are used.

18. The method of claim 14 wherein the region of the electromagnetic spectrum used to perform the chemometric analysis consists of the spectral wavenumber region ranging from about 800 $cm^{-1}$ to about 1800 $cm^{-1}$.

19. The method of claim 14 wherein the analyte is N-(phosphonomethyl)iminodiacetic acid.

20. The method of claim 19 wherein the region of the electromagnetic spectrum used to perform the chemometric analysis consists of the spectral wavenumber region ranging from about 800 $cm^{-1}$ to about 1450 $cm^{-1}$.

21. The method of claim 19 wherein the region of the electromagnetic spectrum used to perform the chemometric analysis consists of the spectral wavenumber region ranging from about 1065 $cm^{-1}$ to about 1400 $cm^{-1}$.

22. The method of claim 14 wherein the analyte is N-(phosphonomethyl)glycine.

23. The method of claim 22 wherein the region of the electromagnetic spectrum used to perform the chemometric analysis consists of the spectral wavenumber region ranging from about 865 $cm^{-1}$ to about 1450 $cm^{-1}$.

24. The method of claim 22 wherein the regions of the electromagnetic spectrum used to perform the chemometric analysis consists of the spectral wavenumber region ranging from about 865 $cm^{-1}$ to about 945 $cm^{-1}$ and the spectral wavenumber region ranging from about 1280 $cm^{-1}$ to about 1460 $cm^{-1}$.

25. The method of claim 14 wherein the analyte is formaldehyde.

26. The method of claim 25 wherein the region of the electromagnetic spectrum used to perform the chemometric analysis consists of the spectral wavenumber region ranging from about 945 $cm^{-1}$ to about 1150 $cm^{-1}$.

27. The method of claim 25 wherein the regions of the electromagnetic spectrum used to perform the chemometric analysis consists of the spectral wavenumber region ranging from about 945 $cm^{-1}$ to about 1115 $cm^{-1}$.

28. The method of claim 25 wherein the region of the electromagnetic spectrum used to perform the chemometric analysis consists of the spectral wavenumber region ranging from about 1000 $cm^{-1}$ to about 1070 $cm^{-1}$.

29. The method of claim 14 wherein the analyte is formic acid.

30. The method of claim 29 wherein the region of the electromagnetic spectrum used to perform the chemometric analysis consists of the spectral wavenumber region ranging from about 1150 $cm^{-1}$ to about 1300 $cm^{-1}$.

31. The method of claim 29 wherein the region of the electromagnetic spectrum used to perform the chemometric analysis consists of the spectral wavenumber region ranging from about 1650 $cm^{-1}$ to about 1800 $cm^{-1}$.

32. The method of claim 29 wherein the regions of the electromagnetic spectrum used to perform the chemometric analysis consists of the spectral wavenumber region ranging from about 1150 $cm^{-1}$ to about 1300 $cm^{-1}$ and the spectral wavenumber region ranging from about 1650 $cm^{-1}$ to about 1800 $cm^{-1}$.

33. The method of claim 29 wherein the region of the electromagnetic spectrum used to perform the chemometric analysis consists of the spectral wavenumber region ranging from about 1710 $cm^{-1}$ to about 1790 $cm^{-1}$.

34. A process for the preparation of an N-(phosphonomethyl)glycine product selected from the group consisting of N-(phosphonomethyl)glycine, a salt thereof or an ester thereof by oxidation of an N-(phosphonomethyl)iminodiacetic acid substrate selected from the group consisting of N-(phosphonomethyl) iminodiacetic acid, a salt thereof or an ester thereof, the process comprising:

contacting said substrate with an oxygen containing gas in the presence of a catalyst for the reaction;

measuring the concentration in real time or substantially real time of an analyte in the reaction mixture using infrared spectroscopy to measure an electromagnetic absorbance spectrum for the reaction mixture effluent over an infrared wavenumber range of from about 200 $cm^{-1}$ to about 5000 $cm^{-1}$, the analyte being selected from a group consisting of n-(phosphonomethyl) iminodiacetic acid, a salt of N-(phosphonomethyl) iminodiacetic acid, an ester of N-(phosphonomethyl) iminodiacetic acid), N-(phosphonomethyl)glycine, a salt of N-(phosphonomethyl)glycine, an ester of N-(phosphonomethyl)glycine), formaldehyde, formic acid, N-methyl-N-(phosphonomethyl)glycine, N-methyl-aminomethylphosphonic acid, or aminomethylphosphonic acid; and, in response to said substantially real time measurement, controlling one or more process effects by adjusting or maintaining the value of one or more independent process variables affecting the conversion of said substrate, the rate of oxidation of formaldehyde, the rate of oxidation of formic acid, the rate of oxidation of N-(phosphonomethyl)glycine product to aminomethylphosphonic acid or salt or ester thereof, the rate of alkylation of N-(phosphonomethyl)glycine to N-methyl-N-(phosphonomethyl)glycine and/or the rate of dissolution of noble metal from a noble metal catalyst.

35. The process of claim 34 wherein the real time or substantially real time measurement of the selected analyte comprises:

using infrared spectroscopy to measure an electromagnetic absorbance spectrum for the reaction mixture effluent over an infrared wavenumber range of from about 200 $cm^{-1}$ to about 5000 $cm^{-1}$.

36. The process of claim 35 wherein said independent process variables are selected from the group consisting of the addition of oxidant to the reaction mixture, the chemical potential of the oxidant in or in contact with the reaction mixture, the rate of removal of oxidant from the reaction mixture, the reaction temperature, the effective catalyst surface area in contact with the reaction mixture, and the intensity of agitation of the reaction mixture.

37. The process of claim 36 further comprising:

continuously introducing the aqueous feed mixture comprising said substrate into a liquid reaction medium;

continuously introducing an oxygen-containing gas into said reaction mixture;

continuously oxidizing said substrate in a continuous reaction zone containing a catalyst for the reaction;

continuously withdrawing a reaction mixture effluent from said continuous reaction zone.

38. A process as set forth in claim 37 wherein said independent variables are selected from the group consisting of the rate of introduction of molecular oxygen into said continuous reaction zone, the rate of withdrawal of gas from said reaction zone, the oxygen partial pressure at a select location within said reaction zone or in contact with said liquid reaction medium; the temperature of said reaction mixture, the rate of introduction of said aqueous feed mixture to said reaction zone, the rate of withdrawal of said reaction mixture from said reaction zone, the amount of catalyst added to said reaction zone, the amount of catalyst removed from said reaction zone, the amount of a supplemental promoter added to the reaction zone and the intensity of agitation of the reaction mixture.

39. The process of claim 37 wherein the conversion of N-(phosphonomethyl)iminodiacetic acid substrate is controlled by adjusting the rate at which the oxygen-containing gas is introduced into the oxidation reaction zone.

40. The process of claim 37 wherein the conversion of N-(phosphonomethyl)iminodiacetic acid substrate is controlled by adjusting an oxygen partial pressure under which the oxidation reaction occurs.

41. The process of claim 37 wherein the conversion of N-(phosphonomethyl)iminodiacetic acid substrate is controlled by adjusting the amount of catalyst contained in the oxidation reaction zone.

42. The process of claim 37 wherein the conversion of N-(phosphonomethyl)iminodiacetic acid substrate is controlled by adding a supplemental promoter to the oxidation reaction zone.

43. The process of claim 37 wherein the conversion of N-(phosphonomethyl)iminodiacetic acid substrate is controlled by adjusting a residence time in which the reaction mixture remains in the continuous reaction zone.

44. The process of claim 36 further comprising:

continuously introducing an aqueous feed mixture comprising said substrate into a liquid reaction medium in a first oxidation reaction zone;

continuously introducing an oxygen-containing gas into the first oxidation reaction zone;

continuously oxidizing said substrate in the first oxidation reaction zone containing a catalyst for the reaction;

continuously withdrawing an intermediate reaction mixture effluent comprising N-(phosphonomethyl) iminodiacetic acid, a salt of N-(phosphonomethyl) iminodiacetic acid, an ester of N-(phosphonomethyl) iminodiacetic acid), N-(phosphonomethyl)glycine, a salt of N-(phosphonomethyl)glycine, an ester of N-(phosphonomethyl)glycine), formaldehyde, formic acid, N-methyl-N-(phosphonomethyl)glycine, N-methyl-aminomethylphosphonic acid; aminomethylphosphonic acid, or mixtures thereof from the oxidation reaction zone;

continuously introducing an intermediate aqueous feed stream into a second oxidation reaction zone containing a catalyst for the reaction, the intermediate aqueous feed stream comprising N-(phosphonomethyl)glycine product and unreacted N-(phosphonomethyl) iminodiacetic acid substrate obtained in the intermediate reaction mixture effluent;

introducing an oxygen-containing gas into the second oxidation reaction zone;

continuously oxidizing said substrate in the second oxidation reaction zone; and, continuously withdrawing a reaction mixture effluent comprising N-(phosphonomethyl)iminodiacetic acid, a salt of N-(phosphonomethyl)iminodiacetic acid, an ester of N-(phosphonomethyl)iminodiacetic acid), N-(phosphonomethyl)glycine, a salt of N-(phosphonomethyl)glycine, an ester of N-(phosphonomethyl)glycine), formaldehyde, formic acid, N-methyl-N-(phosphonomethyl)glycine, N-methyl-aminomethylphosphonic acid, aminomethylphosphonic acid, or mixtures thereof from the oxidation reaction zone;

measuring the concentration in real time or substantially real time of an analyte in the reaction mixture effluent, the analyte being selected from a group consisting of n-(phosphonomethyl)iminodiacetic acid, a salt of N-(phosphonomethyl)iminodiacetic acid, an ester of N-(phosphonomethyl)iminodiacetic acid), N-(phosphonomethyl)glycine, a salt of N-(phosphonomethyl)glycine, an ester of N-(phosphonomethyl)glycine), formaldehyde, formic acid, N-methyl-N-(phosphonomethyl)glycine, N-methyl-aminomethylphosphonic acid, or aminomethylphosphonic acid; and, controlling the conversion of said substrate in the first oxidation reaction zone and/or the second oxidation reaction zone to increase or decrease the concentration of the component measured in the reaction mixture effluent.

45. The process of claim 44 wherein the conversion of N-(phosphonomethyl)iminodiacetic acid substrate in the first oxidation reaction zone is controlled by adjusting the rate at which the oxygen-containing gas is introduced into the first oxidation reaction zone.

46. The process of claim 44 wherein the conversion of N-(phosphonomethyl)iminodiacetic acid substrate in the first oxidation reaction zone is controlled by adjusting an oxygen partial pressure under which the oxidation reaction occurs in the first oxidation reaction zone.

47. The process of claim 44 wherein the conversion of N-(phosphonomethyl)iminodiacetic acid substrate in the first oxidation reaction zone is controlled by adjusting the amount of catalyst contained in the first oxidation reaction zone.

48. The process of claim 44 wherein the conversion of N-(phosphonomethyl)iminodiacetic acid substrate in the first oxidation reaction zone is controlled by adding a supplemental promoter to the first oxidation reaction zone.

49. The process of claim 44 wherein the conversion of N-(phosphonomethyl)iminodiacetic acid substrate in the first reactor reaction zone is controlled by adjusting a residence time for the reaction mixture in the first reaction zone.

50. The process of claim 44 wherein the conversion of N-(phosphonomethyl)iminodiacetic acid substrate in the second oxidation reaction zone is controlled by adjusting the rate at which the oxygen-containing gas is introduced into the second oxidation reaction zone.

51. The process of claim 44 wherein the conversion of N-(phosphonomethyl)iminodiacetic acid substrate in both the first oxidation reaction zone and the second oxidation reaction zone is controlled by adjusting a combined rate at which the oxygen-containing gas is introduced into both the first and second oxidation reaction zones.

52. The process of claim 51 wherein the conversion of N-(phosphonomethyl)iminodiacetic acid substrate in both the first oxidation reaction zone and the second oxidation reaction zone is controlled by adjusting the proportion of the combined rate which is introduced into the first oxidation reaction zone, with the remaining portion of the combined rate being introduced to the second oxidation reaction zone.

53. The process of claim 44 further comprising measuring the concentration in real time or substantially real time of an analyte in the intermediate reaction mixture effluent, the analyte being selected from a group consisting of n-(phosphonomethyl)iminodiacetic acid, a salt of N-(phosphonomethyl)iminodiacetic acid, an ester of N-(phosphonomethyl)iminodiacetic acid), N-(phosphonomethyl)glycine, a salt of N-(phosphonomethyl)glycine, an ester of N-(phosphonomethyl)glycine), formaldehyde, formic acid, N-methyl-N-(phosphonomethyl)glycine, N-methyl-aminomethylphosphonic acid, or aminomethylphosphonic acid; and, controlling the conversion of said substrate in the first oxidation reaction zone to increase or decrease the concentration of the component measured in the intermediate reaction mixture effluent.

54. The process of claim 44 wherein the conversion of N-(phosphonomethyl)iminodiacetic acid substrate in the first reactor reaction zone is controlled by adjusting a residence time for the reaction mixture in the first reaction zone.

* * * * *

UNITED STATES PATENT AND TRADEMARK OFFICE

CERTIFICATE OF CORRECTION

PATENT NO. : 6,818,450 B2 
APPLICATION NO. : 10/150030
DATED : November 16, 2004
INVENTOR(S) : David R. Eaton et al.

It is certified that error appears in the above-identified patent and that said Letters Patent is hereby corrected as shown below:

Column 21, claim 14, line 37, "5000 $cm^{31\ 1}$" should read -- 5000 $cm^{-1}$ --.

(Amendment B Under CFR 1.312, page 4, claim 18, line 13)

Claim 55 was cancelled in Amendment B, but was printed as claim 35 in the issued patent. Further, the dependency of claim 56 printed as claim 36 in the issued patent was amended to depend from claim 54 printed as claim 34 in the issued patent.

Accordingly, please cancel claim 35 at column 23, lines 25-31; and

Column 23, claim 36, line 32, "35" should read -- 34 --.

(Amendment B Under CFR 1.312, page 10, claim 55 and claim 56, line 1)

Signed and Sealed this

First Day of April, 2008

JON W. DUDAS
*Director of the United States Patent and Trademark Office*